US009273349B2

(12) United States Patent
Nguyen et al.

(10) Patent No.: US 9,273,349 B2
(45) Date of Patent: Mar. 1, 2016

(54) DETECTION OF NUCLEIC ACIDS

(71) Applicant: Affymetrix, Inc., Santa Clara, CA (US)

(72) Inventors: Quan Nguyen, San Ramon, CA (US);
Yunqing Ma, San Jose, CA (US);
Audrey Lin, San Jose, CA (US);
Shauna Levinson, Los Gatos, CA (US);
Chunfai Lai, Fremont, CA (US)

(73) Assignee: Affymetrix, Inc., Santa Clara, CA (US)

( * ) Notice: Subject to any disclaimer, the term of this patent is extended or adjusted under 35 U.S.C. 154(b) by 119 days.

(21) Appl. No.: 13/827,392

(22) Filed: Mar. 14, 2013

(65) Prior Publication Data

US 2014/0274756 A1   Sep. 18, 2014

(51) Int. Cl.
*C12Q 1/68* (2006.01)
*C07H 21/00* (2006.01)

(52) U.S. Cl.
CPC ............ *C12Q 1/6841* (2013.01); *C12Q 1/6816* (2013.01)

(58) Field of Classification Search
CPC ...... C12Q 1/68; C12Q 1/6813; C12Q 1/6841; C07H 21/00; C07H 21/02; C07H 21/04
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 4,868,105 A | 9/1989 | Urdea et al. | |
| 5,093,232 A | 3/1992 | Urdea et al. | |
| 5,124,246 A | 6/1992 | Urdea et al. | |
| 5,635,352 A | 6/1997 | Urdea et al. | |
| 5,681,697 A | 10/1997 | Urdea et al. | |
| 5,681,702 A | 10/1997 | Collins et al. | |
| 5,710,264 A | 1/1998 | Urdea et al. | |
| 5,712,383 A | 1/1998 | Sheridan et al. | |
| 5,747,244 A | 5/1998 | Sheridan et al. | |
| 5,780,227 A | 7/1998 | Sheridan et al. | |
| 5,849,481 A | 12/1998 | Urdea et al. | |
| 5,955,272 A * | 9/1999 | Lawrence et al. ............ | 435/6.11 |
| 6,232,462 B1 | 5/2001 | Collins et al. | |
| 6,235,465 B1 | 5/2001 | Kolberg et al. | |
| 6,242,184 B1 * | 6/2001 | Singer et al. ................. | 435/6.14 |
| 6,268,490 B1 | 7/2001 | Imanishi et al. | |
| 6,306,643 B1 | 10/2001 | Gentalen et al. | |
| 6,670,461 B1 | 12/2003 | Wengel et al. | |
| 6,770,748 B2 | 8/2004 | Imanishi et al. | |
| 6,794,499 B2 | 9/2004 | Wengel et al. | |
| 6,852,490 B2 | 2/2005 | Gentalen et al. | |
| 7,033,758 B2 | 4/2006 | Kenny et al. | |
| 7,034,133 B2 | 4/2006 | Wengel et al. | |
| 7,399,845 B2 | 7/2008 | Seth et al. | |
| 7,572,582 B2 | 8/2009 | Wengel et al. | |
| 7,615,351 B2 | 11/2009 | McMaster et al. | |
| 7,709,198 B2 | 5/2010 | Luo et al. | |
| 7,803,541 B2 | 9/2010 | Luo et al. | |
| 7,927,798 B2 | 4/2011 | Zheng et al. | |
| 7,968,327 B2 | 6/2011 | McMaster et al. | |
| 8,017,360 B2 | 9/2011 | Luo et al. | |
| 8,063,196 B2 | 11/2011 | Zheng et al. | |
| 8,114,681 B2 | 2/2012 | Martin et al. | |
| 8,426,578 B2 | 4/2013 | Luo et al. | |
| 8,628,918 B2 | 1/2014 | Luo et al. | |
| 8,632,970 B2 | 1/2014 | Luo et al. | |
| 8,685,753 B2 | 4/2014 | Martin et al. | |
| 2002/0039739 A1 * | 4/2002 | Mack ................................ | 435/6 |
| 2002/0172950 A1 * | 11/2002 | Kenny et al. ...................... | 435/6 |
| 2003/0082807 A1 | 5/2003 | Wengel et al. | |
| 2003/0087230 A1 | 5/2003 | Wengel et al. | |
| 2003/0162955 A1 * | 8/2003 | Chalus et al. ................. | 536/23.5 |
| 2003/0207841 A1 | 11/2003 | Kaneko et al. | |
| 2003/0224377 A1 | 12/2003 | Wengel et al. | |
| 2004/0014959 A1 | 1/2004 | Sorensen et al. | |
| 2004/0143114 A1 | 7/2004 | Imanishi et al. | |
| 2004/0192918 A1 | 9/2004 | Imanishi et al. | |
| 2004/0219565 A1 | 11/2004 | Kauppinen et al. | |
| 2005/0181429 A1 * | 8/2005 | Fejgin et al. ........................ | 435/6 |
| 2007/0172950 A1 * | 7/2007 | Wheeler et al. ............... | 435/458 |
| 2008/0038725 A1 | 2/2008 | Luo et al. | |
| 2009/0081688 A1 | 3/2009 | Luo et al. | |
| 2009/0298709 A1 | 12/2009 | Ma | |
| 2012/0003648 A1 | 1/2012 | Ma et al. | |
| 2012/0004132 A1 | 1/2012 | Zhang et al. | |

(Continued)

FOREIGN PATENT DOCUMENTS

WO        WO 99/14226 A2     3/1999

OTHER PUBLICATIONS

Collins et al., A branched DNA signal amplification assay for quantification of nucleic acid targets below 100 molecules/ml. Nucleic Acids Research 25 (13) : 2979 (1997).*
Fremeau et al., Regulation of Pro-opiomelanocortin Gene Transcription in Individual Cell Nuclei. Science 234 :1265 (1986).*
Gribnau et al., Chromatin interaction mechanism of transcriptional control in vivo. The EMBO Journal 17 (20) : 6020 (1998).*
Van Tine et al., Simultaneous In Situ Detection of RNA, DNA, and Protein Using Tyramide-Coupled Immunofluorescence. Ch.15 in DNA Viruses vol. 292 of Methods in Molecular Biology Ed. By Paul M. Lieberman Humana Press, Inc. (2005).*
Van Tine et al, Simultaneous In Situ Detection of RNA, DNA, and Protein Using Tyramide-Coupled Immunofluorescence. Methods in Molecular Biology 292: 215 (2005).*
Agilent Sureprint Technology (2003) "Content centered microarray design enabling speed and flexibility." Technical note, 12 pp.
Beaucage, Serge L. (2001) "Strategies in the preparation of DNA oligonucleotide arrays for diagnostic applications." *Curr. Med. Chem.*, 8:1213-1244.
Bushnell, et al. (1999) "ProbeDesigner: for the design of probe sets for branched DNA (bDNA) signal amplification assays." *Bioinformatics*, 15(5):348-55.

(Continued)

*Primary Examiner* — Ethan C Whisenant
(74) *Attorney, Agent, or Firm* — Quine Intellectual Property Law Group, P.C.

(57) ABSTRACT

This invention provides compositions, methods, and systems for characterizing, resolving, and quantitating single stranded and double stranded DNA and RNA in-situ. Paired sense and anti-sense probes can signal the presence of double stranded nucleic acids. DNA and RNA can be distinguished in cell and tissue samples by hybridizing with probe sets adapted to highlight differences in these targets in-situ.

8 Claims, 4 Drawing Sheets

(56) References Cited

U.S. PATENT DOCUMENTS

| | | | |
|---|---|---|---|
| 2012/0052498 A1 | 3/2012 | Nguyen et al. | |
| 2012/0172246 A1 | 7/2012 | Nguyen et al. | |
| 2012/0178081 A1 | 7/2012 | Nguyen et al. | |
| 2012/0214152 A1* | 8/2012 | Ma et al. | 435/5 |
| 2014/0024032 A1* | 1/2014 | Raj et al. | 435/6.11 |
| 2014/0357509 A1* | 12/2014 | Ma et al. | 506/9 |

OTHER PUBLICATIONS

Bustin, S.A. (2002) "Quantification of mRNA using real-time reverse transcription PCR (RT-PCR): trends and problems." *J. Mol. Endocrinol.*, 29:23-39.

Bustin and Nolan (2004) "Pitfalls of quantitative real-time reverse-transcription polymerase chain reaction." *J. Biomol. Tech.*, 15:155-166.

Byrom, et al. (2002) "Visualizing siRNA in mammalian cells: Fluorescence analysis of the RNAi effect." *Ambion Tech Notes*, 9 pages.

Collins, et al. (1998) "Branched DNA (bDNA) technology for direct quantification of nucleic acids: Design and performance." *Gene Quantification*, F Ferre, ed., 205-223.

Csaki, et al. (2002) "Gold nanoparticles as novel label for DNA diagnostics."*Expert Rev. Mol. Diagn.*, 2(2):187-93.

Dubertret, et al. (2002) "In Vivo Imaging of Quantum Dots Encapsulated in Phospholipid Micelles." *Science*, 298:1759-1762.

Epstein and Butow (2000) "Microarray technology—enhanced versatility, persistent challenge." *Curr. Opin. Biotechnol.*, 11:36-41.

Flagella, et al. (2006) "A multiplex branched DNA assay for parallel quantitative gene expression profiling." *Anal. Biochem.*, 352(1):50-60.

Jaiswal, et al. (2003) "Long-term multiple color imaging of live cells using quantum dot bioconjugates." *Nat. Biotechnol.*, 21(1):47-51.

Kenny, et al. (2002) "Detection of viral infection and gene expression in clinical tissue specimens using branched DNA (bDNA) in situ hybridization." *J. Histochem. Cytochem.*, 50(9):1219-1227.

Lai, et al. (2012) "Immunofluorescence protects RNA signals in simultaneous RNA-DNA Fish" *Exp. Cell. Res.*, 319(3):46-55.

Nolte (1998) "Branched DNA signal amplification for direct quantitation of nucleic acid sequences in clinical specimens," *Adv. Clin. Chem.*, 33(1):201-235.

Player, et al. (2001) "Single-copy gene detection using branched DNA (bDNA) in situ hybridization," *J. Histochem. Cytochem.*, 49:603-611.

Quantigene® (2007) "2.0 Reagent System" User Manual, 32 pages.

Quantigene® (2011) "ViewRNA ISH Cell Assay" User Manual, 72 pages.

Rose, Don (2000) "Microfluidic Technologies and Instrumentation for Printing DNA Microarrays." *Microarray Biochip Technology*, Schena, Mark, Ed., Biotechniques Books, Natick, MA, 19-38.

Van Cleve, et al. (1998) "Direct quantitation of HIV by flow cytometry using branched DNA signal amplification." *Mol. Cell Probes*, 12:243-247.

Van Tine, et al. (2005) "Simultaneous in situ detection of RNA, DNA, and protein using tyramide-coupled immunofluorescence." *Methods Mol. Biol.*, 292:215-30.

Wahlestedt, et al. (2000) "Potent and nontoxic antisense oligonucleotides containing locked nucleic acids." *Proc. Natl. Acad. Sci. USA*, 97:5633-5638.

Wang, et al. (1997) "Regulation of insulin preRNA splicing by glucose." *Proc. Natl. Acad. Sci. USA*, 94:4360-4365.

Wilber and Urdea (1998) "Quantification of HCV RNA in clinical specimens by branched DNA (bDNA) technology." *Methods Mol. Med.*, 19:71-78.

Wu, et al. (2003) "Immunofluorescent labeling of cancer marker Her2 and other cellular targets with semiconductor quantum dots." *Nat Biotechnol*, 21(1):41-46.

Zhang, et al. (2005) "Small Interfering RNA and Gene Expression Analysis Using a Multiplex Branched DNA Assay without RNA Purification." *J. Biomol. Screen.*, 10(6):549-556.

Antao, et al. (2000) "In Situ Hybridization Using the bDNA Technology." *Techniques in Quantification and Localization of Gene Expression*; Patterson, Bruce, ed.; Birkhauser, Boston; 81-93.

Qian and Lloyd (2003) "Recent Developments in Signal Amplification Methods for In Situ Hybridization." *Diagn Mol Pathol.*, 12(1):1-13.

* cited by examiner

DETECTION OF NUCLEIC ACIDS

FIELD OF THE INVENTION

The present inventions are in the field of nucleic acid detection. The inventions include methods and compositions for detecting double stranded nucleic acids in assay systems and in situ. The inventions also include methods and compositions for simultaneous in situ detection of single stranded DNA and RNA.

BACKGROUND OF THE INVENTION

The presence of nucleic acids in samples has traditionally been determined using Southern blot analyses. However, these methods are limited in typically requiring denaturation of the nucleic acids. Moreover, the old art methods are typically not well adapted to quantitation of the nucleic acids, detection of double stranded nucleic acids versus single stranded nucleic acids, or detection of samples in complex environments, such as tissue samples.

Detection and quantitation of RNA has traditionally been measured using Northern blot, dot blot, and nuclease protection assays. However, these approaches are time-consuming, have limited sensitivity, and the data generated are more qualitative than quantitative in nature. Greater sensitivity and quantification is often possible with polymerase chain reaction (PCR) and reverse transcription PCR (RT-PCR) based methods, such as quantitative real-time RT-PCR, but these approaches have low multiplex capabilities (Bustin (2002) "Quantification of mRNA using real-time reverse transcription PCR (RT-PCR): trends and problems" J Mol Endocrinol 29:23-39 and Bustin and Nolan (2004) "Pitfalls of quantitative real-time reverse-transcription polymerase chain reaction" J Biomol Tech. 15:155-66).

Microarray technology has been widely used in discovery research, but its moderate sensitivity and its relatively long experimental procedure have limited its use in high throughput expression profiling applications (Epstein and Butow (2000) "Microarray technology—enhanced versatility, persistent challenge" Curr Opin Biotechnol. 11:36-41).

Other problems not well addressed in the art are detection of hybridized nucleic acid pairs, localization of certain nucleic acids in complex samples, and simultaneous detection of DNA and mRNA in the same sample.

In Kennedy (J. Histochem & Cytochem 50(9): 1219-1227, 2002; and U.S. Pat. No. 7,033,758), HPV DNAs were detected by in situ hybridizations, e.g., using bDNA technology. The method requires RNAse digestion to avoid possible background and false positive signals from sample RNA sequences. The method was able to distinguish different HPV subtypes and localize the position of the target DNA within a cell. However, the methods were unable to detect RNA or confirm the double stranded status of the nucleic acids.

In Byrom (Ambion Technotes 9(3); Dec. 6, 2004), double labeled, double stranded siRNAs were used to inhibit expression of certain proteins. The siRNAs were stable enough in live host cells to be followed through the course of cell divisions. In one experiment, the anti-sense siRNA strand against c-myc included a red fluorescent reporter, and the sense strand a green fluorescent reporter. Under examination by fluorescence microscope, the double stranded siRNA appeared yellow, e.g., as it was transforming HeLa cells in a cationic lipid carrier. Separated single probe strands were followed, but without any information of their hybridization state.

In view of the above, a need exists for ways to determine the location of certain nucleic acids, and their single or double stranded character. It would be desirable to have systems that can distinguish between DNA and RNA in a cell or tissue sample. The present invention provides these and other features that will be apparent upon review of the following.

SUMMARY OF THE INVENTION

The present inventions involve compositions and methods to detect, characterize and quantitate target nucleic acids of interest, e.g., in assay chips, arrays, and in-situ. For example, compositions are provided wherein paired probes provide signals that distinguish single stranded target nucleic acids from double stranded nucleic acids, in-situ and in vitro. Methods are described herein presenting strategies for using multiple probes to distinguish DNA and RNA in their single stranded and double stranded forms.

A composition useful in distinguishing a single stranded nucleic acid from a double stranded nucleic acid can include paired sense and anti-sense probes, e.g., having different colored signals. For example, the composition can include a first nucleic acid probe comprising a first reporter providing a first signal and comprising a first sequence complementary to a sense strand of a nucleic acid of interest. The composition will also have a second nucleic acid probe comprising a second reporter providing a second signal and comprising a second sequence complementary to an anti-sense strand of the nucleic acid. Typically, the first sequence and second sequence are not complementary to each other, e.g., to avoid unproductive cross-hybridization pairing of probes. In a particularly practical embodiment, the first and second reporters provide signals of different colors, whereby the paired colors are readily distinguished by the human eye, e.g., at a location containing a double stranded nucleic acid of interest.

The composition can further include a nucleic acid encoding the nucleic acid of interest in the double stranded form, e.g., wherein the sense and anti-sense strands of the nucleic acid are hybridized along at least 8 base pairs. For example, the nucleic acid can be in the form of DNA or double stranded RNA. First and second probes can be hybridized to the nucleic acid strands and provide reporter signals of different colors. In many embodiments, the first probe on the sense strand is separated by at lease 10 bases from a sequence on the sense strand having at least 80% identity to a second probe sequence. This can improve desired hybridization kinetics and inherently minimize undesired cross-hybridization between the probes.

The composition, including the probes and nucleic acid can exist in a cell or tissue. For example, a cultured cell lawn or formylin fixed paraffin embedded tissue sample, can be treated with solvents, heat, and/or enzymes to enhance access of probes. The prepared cells or tissues can be exposed to the probes at in hybridization buffers, at appropriate temperatures to specifically hybridize to their target nucleic acid.

Optionally, the composition can function in the context of a solid support having, e.g., one or more capture probes adapted to directly or indirectly bind the nucleic acid of interest through a complementary sequence on the sense or anti-sense strand.

Methods of using the compositions can include hybridizing putative targets with paired probes having different reporting signals, and determining where single or double stranded targets are located. For example, a method of detecting the presence of a double stranded nucleic acid can include providing a first nucleic acid probe comprising a first reporter providing a first signal, and providing a second nucleic acid probe comprising a second reporter providing a second signal. The first probe can have a sequence complementary to a sense strand of a nucleic acid and the second probe can have a sequence complementary to an anti-sense strand of the nucleic acid. It is generally preferred that the first and second probes are not complementary to each other. The first and second probes can be hybridized to a sample comprising a double stranded nucleic acid. The sample can be interrogated to detect signals from the first and/or second probe.

The presence of the double stranded nucleic acid can be confirmed if both the first signal and second signal are detected at the same location (i.e., on the same double stranded region, e.g., associated with a gene sequence). With microscopic detection (e.g., using a fluorescence microscope) single stranded copies of the nucleic acid may appear as yellow or blue signals at certain locations, while double stranded target may appear as a combined green signal to the eye at other locations.

Systems for practicing the methods are considered part of the present inventions. For example, systems can be employed using the compositions of the invention to detect DNA and/or RNA in single or double stranded form. Systems can be configured to simultaneously detect the nucleic acids in an array or in-situ in a tissue. For example, a system for simultaneous detection of DNA and RNA by in-situ hybridization can include a DNA specific probe set with more probes and covering more target sequences than the RNA probe set in the in the system. In certain embodiments, the DNA probe set can comprise more than 50 probes complementary to a DNA gene sequence, while the RNA specific probe set comprises 50 or fewer probes complementary to the RNA sequence. In certain embodiments, the DNA probe set can comprise at least 3-fold more different probes, e.g., covering at least 3-fold more sequence than the RNA specific probe set of the system. The DNA probes each have different probe sequences (to different target sequences) and the RNA probes each have different probe sequences. Such proportioning of more DNA probes and fewer RNA probes can help confirm that a signal is from a DNA or RNA target, e.g., in tissue hybridizations wherein we have found signals much easier to generate against RNA than DNA. For example, even if the RNA probes were against mRNA coded by the DNA, the adaptation of lower numbers of RNA probe can provide a significant signal over background for any of the mRNA in the sample, while remaining undetectable against background for the less efficient DNA hybridizations in the same sample.

Confidence in distinguishing DNA and RNA in-situ can be increased, e.g., by adapting the DNA probes to provide a first detectable signal, and adapting the RNA probes to provide a second detectable signal. In certain preferred embodiments, the DNA first and RNA second signals are different signals.

It can be desirable to proportion the expected DNA and RNA signals so they are readily detected under the same conditions. We find that for most detection parameters, DNA targets in cells and tissues provide at least 3-fold less signal than similar (e.g., same sequence) RNA in the same cell or tissue. Therefore, it can be desirable to take steps to relatively raise the detection of DNA when one is simultaneously analyzing such samples for both DNA and RNA. For example, in many instances the DNA of interest can be probed with a DNA probe set having at least 100 different probes (e.g., label extender pairs) and/or covering at least 50 kilobases of the DNA (e.g., gene) sequence. Meanwhile, the RNA of interest (e.g., having the same coding sequence as the DNA of interest) can be probed with an RNA probe set having 30 or fewer different probes and/or cover not more than about 1.5 kilobases of the mRNA sequence.

Methods can include the technique of determining the minimum DNA probe number and/or probe set coverage to provide a signal above background. Further, the minimum RNA probe number and/or probe set coverage to provide a signal above background for RNA target, or avoiding a signal above background for a DNA target, can be determined. With this information, RNA probe sets can be configured to signal RNA but not DNA, even where the probes complement both DNA and RNA sequences.

To further improve the ability of the probe systems to distinguish between DNA and RNA targets, a variety of techniques, including those above, can be combined to progressively enhance the sensitivity and specificity of the analyses. For example, the DNA probes can have sequences complementary to an anti-sense strand of the gene of interest and the RNA probes can comprise sequences complementary to coding regions of the gene. Optionally, the DNA probes can have reporters providing signals different from those of the RNA probes. Optionally, RNA sequence of the target RNA is encoded by the translated gene sequence.

Probe systems with relatively high specificity for DNA can be prepared as described above. DNA specificity can also be provided by a combination of other features, such as selecting the DNA probe sequence based on a gene intron sequence or the complement of a gene exon sequence. Further, the DNA probes can avoid possible RNA targeting by basing their sequences on intron sequences, anti-sense sequences, regulatory sequences, and non-coding sequences.

Methods for detecting DNA or RNA in-situ can include probing with DNA and RNA probes selected to take advantage of differences in accessibility, differences reading frame, differences in strandedness, differences in the imaged shape of signals, and/or differences in signal location within a sample. For example, methods for distinguishing DNA and RNA in-situ can include providing a DNA specific probe set comprising more (e.g., 50+ probes) complementary to a DNA gene sequence, wherein the DNA probes are adapted to provide a first detectable signal; providing an RNA specific probe set comprising fewer (e.g., 1 to 50) probes complementary to an mRNA sequence, wherein the RNA probes are adapted to provide a second detectable signal. Then, hybridizing the DNA probe set and RNA probe set (e.g., simultaneously) to a sample of interest. Finally, the sample can be interrogated for DNA and/or RNA specific signals. If a signal is detected over background from the RNA probe set, the presence of mRNA is indicated. Even if there were DNA with a complementary sequence present, it would not provide adequate signal over background for a positive result. However, if at the same time the sample was hybridized with the DNA probe having a different reporter signal, the DNA could be visualized in the same detection.

Optionally, the presence of DNA and RNA at separate locations of the same sample could be identified, by first hybridizing with the RNA probe, then hybridizing with the DNA probe. Initially, detectable signals would be assigned as RNA locations, while locations only reporting with the DNA probes would be assigned as DNA locations. In some embodiments, RNA would be detected by a probe sets with fewer probes and less coverage, than DNA would be identified with an expanded probe set with more probes and greater coverage. DNA and transcribed RNA could be further distinguished by using different reporter signals for the DNA probe set as compared to the mRNA probe set.

DEFINITIONS

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular compositions, methods, or systems, which of course, can vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a component" can include a combination of two or more components; reference to "a nucleic acid" can include mixtures of nucleic acids, and the like.

Although many methods and systems similar, modified, or equivalent to those described herein can be used in the practice of the present invention without undue experimentation, many preferred materials and methods are described herein. In describing and claiming the present invention, the following terminology will be used in accordance with the definitions set out below.

The term "about" as used herein indicates the value of a given quantity varies by +/−10% of the value, or optionally +/−5% of the value, or in some embodiments, by +/−1% of the value so described.

Branched DNA (or "bDNA") technology used in the methods can include amplification methods that employ label systems that hybridize directly or indirectly to a target nucleic acid and associate multiple copies of another nucleic acid (e.g., label probes) to the target nucleic acid. It is worth noting that an amplification multimer of a bDNA assay is typically, but not necessarily, a branched-chain nucleic acid; for example, the amplification multimer can be a branched, forked, or comb-like nucleic acid or a linear nucleic acid, or a complex thereof. Typically branched DNA of the present invention includes a nucleic acid having a "trunk" structure covalently attached to multiple nucleic acid branches having multiple sequences complementary to, e.g., label probes. For example, see amplification multimers described herein. Alternately, the branches of the branched DNA label systems can be attached to a "trunk" by affinity or hybridization systems to ultimately associate the multiple sequences to the target nucleic acid. For example, see labeling systems, described herein, comprising label extenders complementary to preamplifiers complementary to amplifiers complementary to label probes.

The term "amplification" in the context of the present inventions, refers to an accumulation of two or more molecules in a system, which accumulation is specifically associated with the presence of a nucleic acid of interest (e.g., target nucleic acid of a sample) in the system (e.g., in-situ or at a surface). The accumulation can consist of enzymatic replication of copies the nucleic acid of interest. Alternately, the amplification can consist of an accumulation of another molecule (e.g., binding an amplification product nucleic acid to a solid support) dependent on the presence of the nucleic acid of interest. For example, in a typical bDNA assay, the presence of a target nucleic acid of interest in the system can be amplified into a large number of detectable label probes bound to a solid support in association with the initial presence of the target nucleic acid in a sample.

The term "polynucleotide" (and the equivalent term "nucleic acid") encompasses any physical string of monomer units that can be corresponded to a string of nucleotides, including a polymer of nucleotides (e.g., a typical DNA or RNA polymer), peptide nucleic acids (PNAs), modified oligonucleotides (e.g., oligonucleotides comprising nucleotides that are not typical to biological RNA or DNA, such as 2'-O-methylated oligonucleotides), and the like. The nucleotides of the polynucleotide can be deoxyribonucleotides, ribonucleotides or polymers of nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. In one aspect, the nucleotide analogs can be a locked nucleic acid analog such as the constrained ethyl (cEt) nucleic acid analog. Various bicyclic nucleic acid analogs have been prepared and reported. (See, for example, Singh et al., Chem. Commun., 1998, 4:455-456; Koshkin et al., Tetrahedron, 1998, 54:3607-3630; Wahlestedt et al., Proc. Natl. Acad. Sci. U.S.A., 2000, 97:5633-5638; Kumar et al., Bioorg. Med. Chem. Lett., 1998, 8:2219-2222; Wengel et al., PCT International Application Number PCT/DK98/00303 which published as WO 99/14226 on Mar. 25, 1999; Singh et al., J. Org. Chem., 1998, 63:10035-10039, the text of each is incorporated by reference herein, in their entirety). Examples of issued US patents and Published U.S. patent applications disclosing various bicyclic nucleic acids include, for example, U.S. Pat. Nos. 6,770,748, 6,268,490 and 6,794,499 and U.S. Patent Application Publication Nos. 20120052498; 20040219565, 20040014959, 20030207841, 20040192918, 20030224377, 20040143114, 20030087230 and 20030082807, the text of each of which is incorporated by reference herein, in their entirety. The polynucleotide can additionally comprise non-nucleotide elements such as labels, quenchers, blocking groups, or the like. The polynucleotide can be, e.g., single-stranded or double-stranded.

A "polynucleotide sequence", "nucleic acid sequence", or "nucleotide sequence" is a polymer of nucleotides (an oligonucleotide, a DNA, an RNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Two polynucleotides "hybridize" when they associate to form a stable base pair aligned duplex, e.g., under relevant assay conditions. Nucleic acids hybridize due to a variety of well characterized physico-chemical forces, such as hydrogen bonding, solvent exclusion, base stacking, and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, New York).

The "Tm" (melting temperature) of a nucleic acid duplex under specified conditions (e.g., relevant assay conditions) is the temperature at which half of the base pairs in a population of the duplex are disassociated and half are associated. The Tm for a particular duplex can be calculated and/or measured, e.g., by obtaining a thermal denaturation curve for the duplex (where the Tm is the temperature corresponding to the midpoint in the observed transition from double-stranded to single-stranded form).

The term "complementary" refers to a polynucleotide that forms a stable duplex with its "complement," e.g., under relevant assay conditions. Typically, two polynucleotide sequences that are complementary to each other have mismatches (mismatched base pairs) at less than about 20% of the bases, at less than about 10% of the bases, preferably at less than about 5% of the bases, one mismatch, and more preferably have no mismatches.

A "capture probe" or "CP" is a polynucleotide attached to a solid support and comprises a sequence useful to directly or indirectly specifically capture a particular nucleic acid of interest. For example, a capture probe can specifically hybridize to a capture extender (and/or can include a sequence complementary to a nucleic acid of interest, e.g., to directly and specifically capture the nucleic acid of interest) and that is tightly bound (e.g., covalently or non-covalently, directly or through a linker, e.g., streptavidin-biotin or the like) to a solid support, a spatially addressable solid support, a slide, a particle, a microsphere, a bead, or the like. The capture probe typically comprises at least one polynucleotide sequence C-2 that is complementary to polynucleotide sequence C-1 of at least one capture extender (or, in systems designed for direct capture of a nucleic acid of interest, the C-2 sequence can be complementary to a sequence of the nucleic acid of interest). The capture probe is preferably single-stranded.

A "capture extender" or "CE" is a polynucleotide (or comprises a polynucleotide) that is capable of hybridizing to a nucleic acid of interest and to a capture probe. A capture extender can bind a particular nucleic acid of interest to a particular solid support, through a capture probe, with high specificity. The capture extender typically has a first polynucleotide sequence C-1, which is complementary to the capture probe, and a second polynucleotide sequence C-3, which is complementary to a polynucleotide (target) sequence of the nucleic acid of interest. Sequences C-1 and C-3 are typically not complementary to each other. The capture extender is preferably single-stranded.

A "label extender" or "LE" is a polynucleotide that is capable of hybridizing to a target nucleic acid of interest and to a label probe system. A capture extender can link a particular nucleic acid of interest to components of a label system. The label extender typically has a first polynucleotide sequence L-1, which is complementary to a polynucleotide sequence of the nucleic acid of interest, and a second polynucleotide sequence L-2, which is complementary to a polynucleotide sequence of the label probe system (e.g., L-2 can be complementary to an M-1 polynucleotide sequence of an amplification multimer, a preamplifier, a label probe, or the like). The label extender is preferably single-stranded.

A "label" is a moiety that facilitates detection of a molecule (e.g., by providing a detectable signal). Common labels in the context of the present invention include fluorescent, luminescent, light-scattering, and/or colorimetric labels. Suitable labels include enzymes and fluorescent moieties, as well as radionuclides, substrates, cofactors, inhibitors, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Many labels are commercially available and can be used in the context of the invention.

A "label probe" or "LP" is a single-stranded polynucleotide that comprises a label (or optionally that is configured to bind to a label) that directly or indirectly provides a detectable signal. The label probe typically comprises a polynucleotide sequence that is complementary to the repeating polynucleotide sequence M-2 of an amplification multimer. Optionally, a label probe can hybridize directly to a sequence on the nucleic acid of interest. However, in most cases, label probes are not designed to hybridize directly to the nucleic acid of interest.

A "label probe system", in the context of the present inventions, comprises one or more polynucleotides that can hybridize (through a label extender or not), to associate one or more labels with a nucleic acid of interest. The nucleic acid of interest can be, e.g., a target nucleic acid of interest in a sample. For example, a label probe system can comprise a combination of label extenders, amplification multimers, preamplifiers, amplifiers, and/or label probes. In one embodiment, the label probe system comprises an amplification multimer with an M-1 sequence complementary to a label extender and a plurality of M-2 sequences complementary to a label probe sequence. Optionally, the label probe system comprises a preamplifier with a sequence complementary to a label extender L-2 sequence and replicate sequences complementary to an amplifier sequence, which amplifier also has replicate sequences complementary to a label probe sequence. One or more polynucleotide sequences M-1 of the label probe system are optionally identical sequences or different sequences. Optionally, the label probe system hybridizes directly to a nucleic acid of interest without a label extender. Alternately, the label probe system is simply a label probe with a sequence complementary to a nucleic acid of interest (or not). The label probe system can include a plurality of label probes (e.g., a plurality of identical label probes, probes of different types, or probes of the same type but providing different detectable signals).

As used herein, the term "reporter" refers to a component, as known in the art that can be used to identify and/or detect an associated molecule of interest. For example, reporter can be a fluorescent or colored chemical moiety, or a radioactive isotope. A reporter can include a protein, e.g., an enzyme, that confers antibiotic resistance or sensitivity (e.g., β-lactamase, chloramphenicol acetyltransferase (CAT), and the like), a fluorescent screening marker (e.g., a green fluorescent protein (e.g., (GFP), YFP, EGFP, RFP, etc.), a luminescent marker (e.g., a firefly luciferase protein), an affinity based screening marker, or positive or negative selectable marker genes. A reporter can include a nucleic acid which when present confirms the presence of another associated (e.g., through hybridization) nucleic acid. Often, in the context of bDNA detections, in-situ visualizations and array detections, the reporter is a fluorescent group. Typically, in a bDNA assay, a reporter is directly or indirectly bound to a nucleic acid as an element of a label probe.

As used herein, a "gene" is a locatable region of genomic sequence providing information for expression of a particular polypeptide. The gene can include the sense and anti-sense strands, and coding (e.g., exon) and non-coding (e.g., intron, regulatory) regions.

As used herein, the term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

A "sense" strand of a nucleic acid is a strand that read 5' to 3' provides the triplet code that identifies the peptide sequence of the polypeptide encoded by the nucleic acid. A DNA gene encodes its associated polypeptide. As is known in the art, the DNA also provides the anti-sense template from which a sense mRNA copy of the encoding DNA is transcribed. Often, the DNA gene sense strand includes both expressed encoding sequence segments (exons) and non-encoding sequence segments (introns).

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

"In-situ" as used herein means to examine the phenomenon exactly in place where it occurs. For example, to study the presence, location, character, and quantity of a particular nucleic acid in a tissue or cell, in-situ would be in the tissue or cell. This contrasts with detections in laboratory equipment substrates, e.g., in vitro, wherein the target nucleic acids are in solution, on beads, in an array, etc.

A "complex" in the context of amplifications of the invention, refers to three or more amplification components (e.g., capture probes, capture extenders, label extenders, amplification multimers, preamplifiers, or label probes) bound together through hybridization of complementary sequences.

"Different" polynucleotides have different sequences. For example, a polynucleotide or polynucleotide sequence is different from another if they do not have 100% sequence identity, have less that 99% identity, less that 95% identity less than 90% identity or less than 80% sequence identity. "Different" with respect to reporter signals can include signals that can be distinguished by the applicable detector system. For example, the human eye can distinguish the difference between green and red light waves. However, there comes a point where two colors are not exactly the same wavelengths, yet are so similar that the human eye can not detect the difference. "Different locations" with regard to detection of signals refers to signals emanating from probes hybridized to the same nucleic acid molecule. For signals from an in-situ hybridization of a cell or tissue are in the same location if they appear to come from (are detected as) the same intracellular location on microscopic examination. Where probes of with different signals are resolved to appear in the same intracellular location (e.g., portion of the nucleus or cytoplasm), yet appear as a mixed (unresolved) signal the signals are in the same location (e.g., not in different locations).

Polynucleotides are "captured" when they are bound directly or indirectly (e.g., through hybridization to an extender or as part of a complex) to a solid support.

Polynucleotides are "indirectly" associated (e.g., hybridized, captured, bound) with a solid support or another identified polynucleotide when the association comprises linkage through one or more other polynucleotide, such as, e.g., a capture extender or label extender.

An "amplification multimer" is as known in the mature art of bDNA analyses. An amplification multimer is a polynucleotide comprising a sequence directly complementary to a nucleic acid of interest (or indirectly specifically hybridizable to the nucleic acid of interest, e.g., through a label extender) and comprising a plurality of substantially identical polynucleotide sequences complementary to label probes. The amplification multimer has a structure designed to function by specifically associating multiple label probes with a nucleic acid of interest. For example, amplification multimers can have an M-1 polynucleotide sequence complementary to a nucleic acid of interest and a plurality of M-2 sequences complementary to label probes, e.g., to specifically bind multiple labels to the nucleic acid of interest. The M-1 sequence of the amplification multimer is not necessarily attached to the replicate M-2 sequences solely through covalent bonds (i.e., M-2 sequences of an amplification multimer can be associated with M-1 sequences through non-covalent interactions, such as, e.g., polynucleotide hybridizations, affinity interactions, and/or the like). For example, an amplification multimer can comprise a preamplifier complementary to a label extender (or target nucleic acid) and an amplifier complementary to the preamplifier and multiple label probes. The amplification multimer can be, e.g., a linear or a branched nucleic acid. As noted for all polynucleotides, the amplification multimer can include modified nucleotides and/or non-standard internucleotide linkages as well as standard deoxyribonucleotides, ribonucleotides, and/or phosphodiester bonds. Suitable amplification multimers are described, for example, in U.S. Pat. No. 5,635,352, U.S. Pat. No. 5,124,246, U.S. Pat. No. 5,710,264, and U.S. Pat. No. 5,849,481.

A "preamplifier" is a nucleic acid that serves as an intermediate between one or more label extenders and amplifiers. Typically, the preamplifier is capable of hybridizing simultaneously to at least two label extenders and to a plurality of amplifiers.

DETAILED DESCRIPTION

Figure 1:
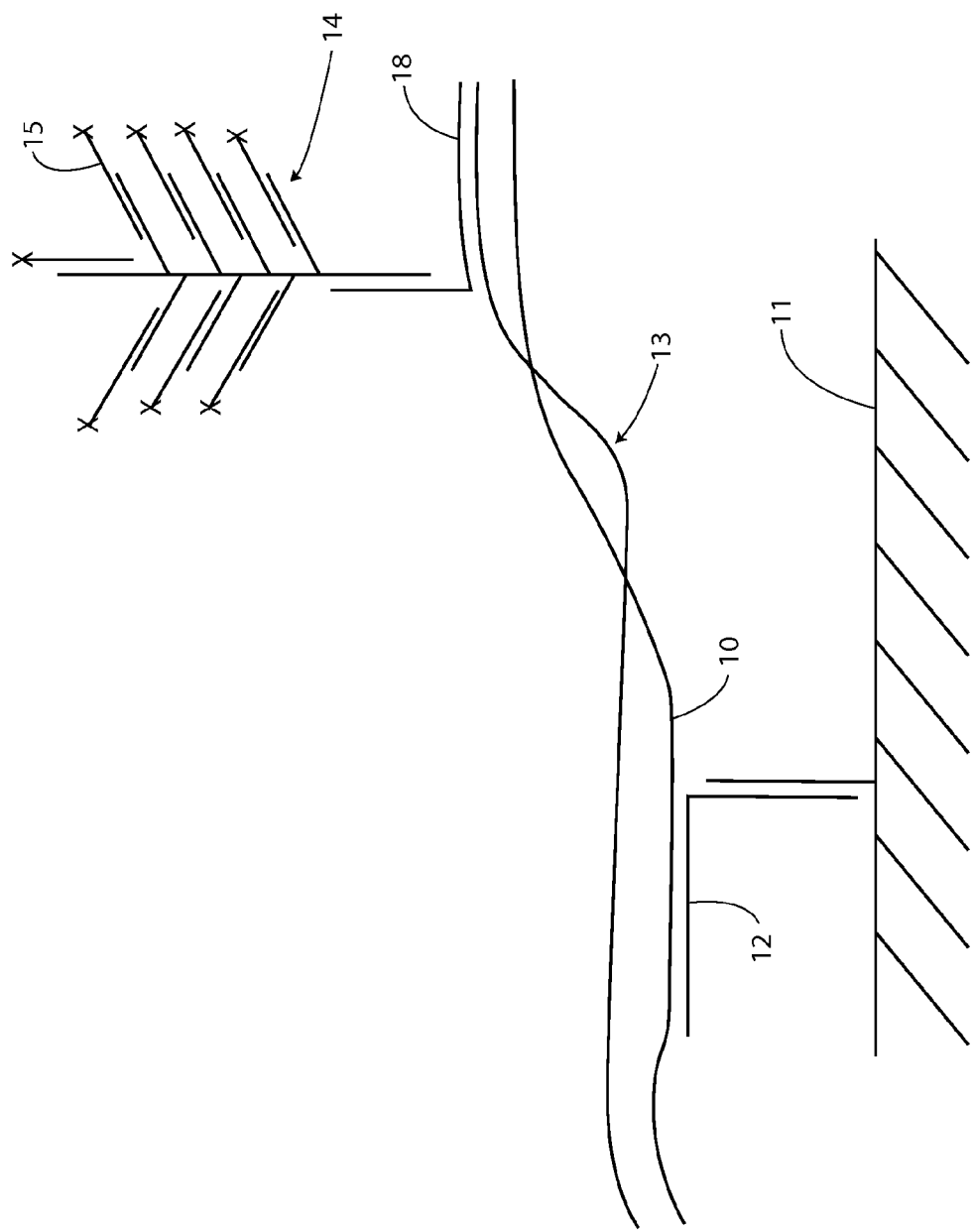
FIG. 1 shows a schematic example of double stranded nucleic acid detection on a solid support, using a first strand capture and a second strand probe signal.

The present inventions provide compositions and techniques useful in analysis of nucleic acid detection, imaging, and quantitation in situ and on substrates. The methods can be configured to detect single or double stranded DNA or RNA. In many embodiments, the methods are capable of confirming a sequence is associated with a double stranded nucleic acid.

Compositions for Detection of Double Stranded Nucleic Acids

The inventive compositions include, e.g., nucleic acid probes with different reporting groups and configured to hybridize to separate strands of a double stranded nucleic acid. For example, the double stranded nucleic acid detector probes can include a combination of sense and anti-sense probes that are not complements, so they don't hybridize to each other. In many embodiments, the sense and anti-sense probes provide different reporter signals, e.g., different visible colors. The compositions include the probes in combination with the target gene of interest, e.g., in a cell or on the solid support of an array of assay device.

Probes of the Compositions

Probes of the compositions include one or more nucleic acid probes complementary to sequences on the sense strand of a gene of interest, and one or more nucleic acid probes complementary to sequences on the anti-sense strand of the gene. Typically, the probes comprise reporters that provide different signals for the sense and anti-sense probes.

The nucleic acid probes of the compositions and methods herein can be simple label probes (e.g., consisting of a targeting sequence with a reporter group) or more complex structures, e.g., with intermediary hybridization amplification structures between the targeting complimentary sequence and the reporter. For example, the nucleic acid probe system can include a bDNA amplification system components, such as label extenders, preamplifiers, and/or amplification multimers, e.g., ultimately directly or indirectly hybridized to multiple label probes in a complex. In certain embodiments, the probes are not PCR probes.

In most embodiments, the probes are designed not to overlap each other along the sequence of the nucleic acid target of interest. That is, nucleic acid sequences of the probes should not ordinarily find a complementary sequence among the sequences of the other probes. This can help ensure the probes do not form pairs with each other, but only hybridize with the intended target nucleic acid.

Probes employed in the present compositions can be any suitable to the intended nucleic acid target, sample type, and intended detection technique. In a rather simple form, the probes are merely nucleic acid oligomers with unique sequences detectable by standard techniques, e.g., such as blotting, PCR, FRET, fluorometry, and bDNA analysis. In a more common embodiment, the probes can be oligonucleotides with sequences complementary to the nucleic acid of interest and comprising a reporter group (as discussed below), e.g., a chromogen or fluorescent detectable moiety. In bDNA embodiments, the probes can be an amplification multimer with a sequence complement (M-1 sequence) to the nucleic acid of interest and/or a sequence interacting with an amplification multimer (through a label extender L-1 sequence).

The probe sequence complement to the target can be designed to hybridize strongly enough with the target sequence to provide an adequate signal over background, under conditions of the elected detection system. For example, the probes can range in length from about 5 bases to more than 5 kb, from 6 bases to 2 kb, from 7 bases to 1 kb, from 8 bases to 500 bases, from 10 bases to 250 bases, from 15 bases to 100 bases from 20 bases to 100 bases or about 25 bases. The percent identity required can vary with the length of the probe and the hybridization conditions, as is known in the art. For example, the probes can range from percent identify with the target sequence from less than about 50% to 100% identity, from about 70% to 99%, from 80% to 98%, from 90% to 97%, or about 95%. Typically, complete identity provides the best results with probes, but less than perfect identity can provide adequate signal to background, e.g., where hybridization conditions are properly adjusted or where there is little complementarity with non-target sequences in a given sample.

The sense direction is 5'-3' along the nucleic acid strand that encodes the gene of interest. That is, e.g., reading the triplet code on the sense strand 5'-3' provides the amino acid sequence of the protein of interest. A sense probe comprises a sequence that complements and hybridizes with the sense strand. For example, a sense probe will have at least a section of anti-sense sequence, e.g., capable of hybridizing to the complementary sense strand sequence under at least stringent hybridization conditions.

The anti-sense strand is the complement of the encoding sense strand in a double stranded nucleic acid. An anti-sense probe comprises a sequence that complements and hybridizes with the anti-sense strand. For example, an anti-sense probe will have at least a section of sense sequence, e.g., capable of hybridizing to the complementary sense strand sequence under at least stringent hybridization conditions.

When sense and anti-sense probes are hybridized to the target nucleic acid, they are aligned opposite directions on the double stranded DNA, e.g., relative to the coding reading frame. It is possible that the sense and anti-sense probes could complement each other, e.g., by having sequences complementary to target sequences along a common segment of the target double stranded nucleic acid. However, this could lead to undesirable probe pairing that wastes probes and could generate undesirable background or false positive signals. In preferred embodiments, the sequences of sense and anti-sense probes are not substantially complementary, e.g., not hybridizing under stringent hybridization conditions (as described below).

In one aspect of the inventive compositions, the sense and anti-sense probes can have reporter groups that provide different signals. Using such probes, one can determine if a signal is coming from a sense probe or from an anti-sense probe. Further, in samples with both sense and anti-sense target strands, the different signals can be used to determine if the sense and anti-sense strands are at the same or different locations. The signals can be any appropriate to the means of detection employed. For example, the probes can present different color absorbance, different color fluorescence, and/or different isotope radiation. Color signals can be in the visible range, or outside the visible range, e.g., detectable by commonly available light detectors, such as charge coupled devices (CCD), photomultiplier tubes (PMT), active pixel sensors (APS), photographic film, photodiodes, and/or the like. In preferred embodiments, the signals are in the visible range of a human eye, e.g., so that sense, ant-sense and mixed signals are readily detected by observation by a technician, e.g., using a microscope or standard video devices.

Probes and detection systems of the present compositions and methods can beneficially incorporate bicyclo[3.3.0] nucleosides (bcDNA) within polynucleotides. Oligonucleotides containing these analogues have been found to form Watson-Crick bonded duplexes with complementary DNA and RNA oligonucleotides. bcDNA oligomers exhibit an increase in sensitivity to the ionic strength of the hybridization media compared to natural counterparts. The bicyclo analogs can influence the Tm of hybridization allowing adjustment of oligomer melting temperatures to conform to overall hybridization schemes in bDNA complexes. Various modifications of these analogs can exhibit desired properties of being stably integrated into oligonucleotide sequences and increasing the melting temperature at which hybridization occurs, thus producing a very stable, energy-minimized duplex with oligonucleotides comprising even native nucleic acids. (See, for instance, U.S. Pat. Nos. 7,572,582, 7,399,845, 7,034,133, 6,794,499 and 6,670,461, all of which are incorporated herein by reference in their entirety for all purposes).

In preferred embodiments, pairs of sense/anti-sense probes provide signals of different primary colors. For example, paired probes can have different colors from cyan, magenta, and yellow, or from red, green, and blue. In this way, separate sense or anti-sense probes are uniquely and distinctly visible, while combinations of sense and anti-sense probes can be visually sensed as associated secondary colors. For example, where the paired sense and anti-sense probes are red and blue, the probes at the same detected location can appear as a violet signal; magenta and yellow as orange, etc., as is known in the art. In many embodiments, the "colors" are provided by fluorescent small molecule labels, fluorescent protein tags, and/or enzymes in combination with their chromogenic substrate. Colored reporters can be covalently bound to the probes, or indirectly associated with the probes, e.g., by hybridization or antibody interaction.

Nucleic acid sequences can be targets of interest in the compositions with sense and/or anti-sense probes. The nucleic acids can be any type of interest, such as, e.g., DNA, cDNA, mitochondrial DNA, rRNA, mRNA, miRNA, etc. However, in certain embodiments, the compositions are especially well adapted to analysis of double stranded nucleic acids (e.g., dsRNA and dsDNA), including, e.g., sense and anti-sense strands of gene sequences. The probes can detect, locate, and characterize nucleic acids of interest with high sensitivity from complex sample materials.

Samples

Samples can be analyzed in vivo, in vitro and in-situ using the present compositions. The compositions can be used to detect the presence of the nucleic acids of interest in essentially any type of sample. For example, putative nucleic acids of interest in a sample can be derived from an animal, a human, a plant, a cultured cell, a virus, a bacterium, a pathogen, and/or a microorganism. The samples for analysis can be genetically engineered or synthesized. The sample optionally includes a cell lysate, an intercellular fluid, a bodily fluid (including, but not limited to, blood, serum, saliva, urine, sputum, or spinal fluid), and/or a conditioned culture medium, and is optionally derived from a tissue (e.g., a tissue homogenate), a biopsy, and/or a tumor. As just a few examples, the nucleic acids of interest can be derived from one or more of an animal, a human, a plant, a cultured cell, a microorganism, a virus, a bacterium, or a pathogen. In many cases, the use of a bDNA type amplification can have a great advantage over many enzymatic amplifications (e.g., PCR) for such complex and impure samples because hybridizations are less sensitive to interference than typical amplification enzymes. With the bulk of the complex sample washed away after the first amplification, the first amplification product can be far more compatible with second amplification systems, including enzymatic amplification systems.

Figure 3:
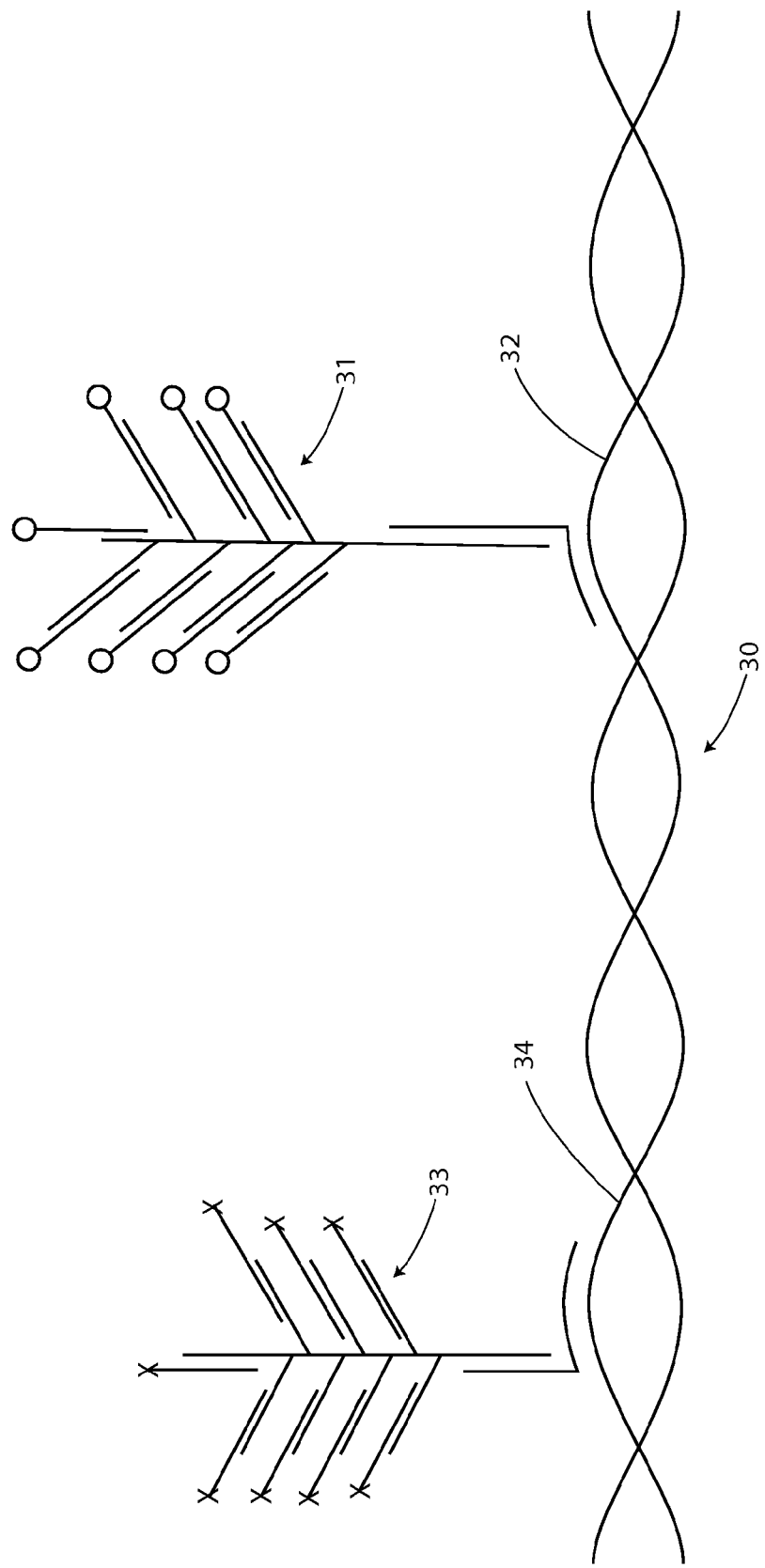
FIG. 3 illustrates a technique for detecting a particular double stranded nucleic acid in-situ using a first strand probe signal and a second strand probe signal.

The compositions can be used to probe cells and tissues in-situ for nucleic acids of interest. For example, see FIG. 3, and description below in Example 2. Cells on a slide, cells processed with a flow cytometer, or formalin fixed paraffin embedded (FFPE) tissues, can be analyzed as part of the inventive compositions. The cell or tissues are typically fixed and rendered permeable before hybridization with the probes, to retain the nucleic acid targets in the sample and permit the probes and hybridization buffers to enter the cells. Double-stranded nucleic acid targets can be fully or partially denatured before hybridization with the probes. In fixed tissue samples, double stranded target strands can be completely melted apart, while remaining at the same location of the sample, thereby still presenting confirmation of their previous double stranded condition on later probing.

The compositions can also be employed in a solid support format. For example, instead of detecting double stranded nucleic acids fixed in a tissue, probes can interrogate nucleic acids captured on a solid support. For example, see FIG. 1 and description in Example 1. Samples for analysis could be complex mixtures, such as lysates bound to nitrocellulose, or array members of a library on an array. In one embodiment, the composition includes single and/or double stranded nucleic acids specifically bound to a solid support location through, e.g., capture probes or capture extenders. In such a case, each strand of a double stranded nucleic acid could be captured by proximate capture extenders, or only one strand could be captured with the second strand held by at least one unmelted segment (e.g., 4 to 20 bases, 6 to 15 bases, or about 8 contiguous unmelted base pairs) between the two strands (see FIG. 2).

Methods for Detection of Double Stranded Nucleic Acids

The compositions described above can be employed in methods to detect, localize and/or quantitate single and double stranded nucleic acids of interest. For example, a sample with a putative nucleic acid of interest can be hybridized to a pair of sense and anti-sense probes to ultimately generate signals informing where single and/or double stranded copies of the nucleic acid are present.

In general, the methods can include the steps of, e.g., providing a sense first probe and a anti-sense second probe, each probe having different reporting groups; hybridizing the probes to a sample; and, detecting first and/or second signals. A sense strand is found where a first reporter signal is located, an anti-sense strand is found where a second reporter signal is located, and double stranded nucleic acid found at a location where both signals are detected. As compared to prior art assays, each single strand and double stranded condition can be detected simultaneously, according to these methods. Further, the combination of first and second signals from the same location can be sensed as a unique readily identified combined signal, e.g., apparent as a different color on sight.

Figure 4:
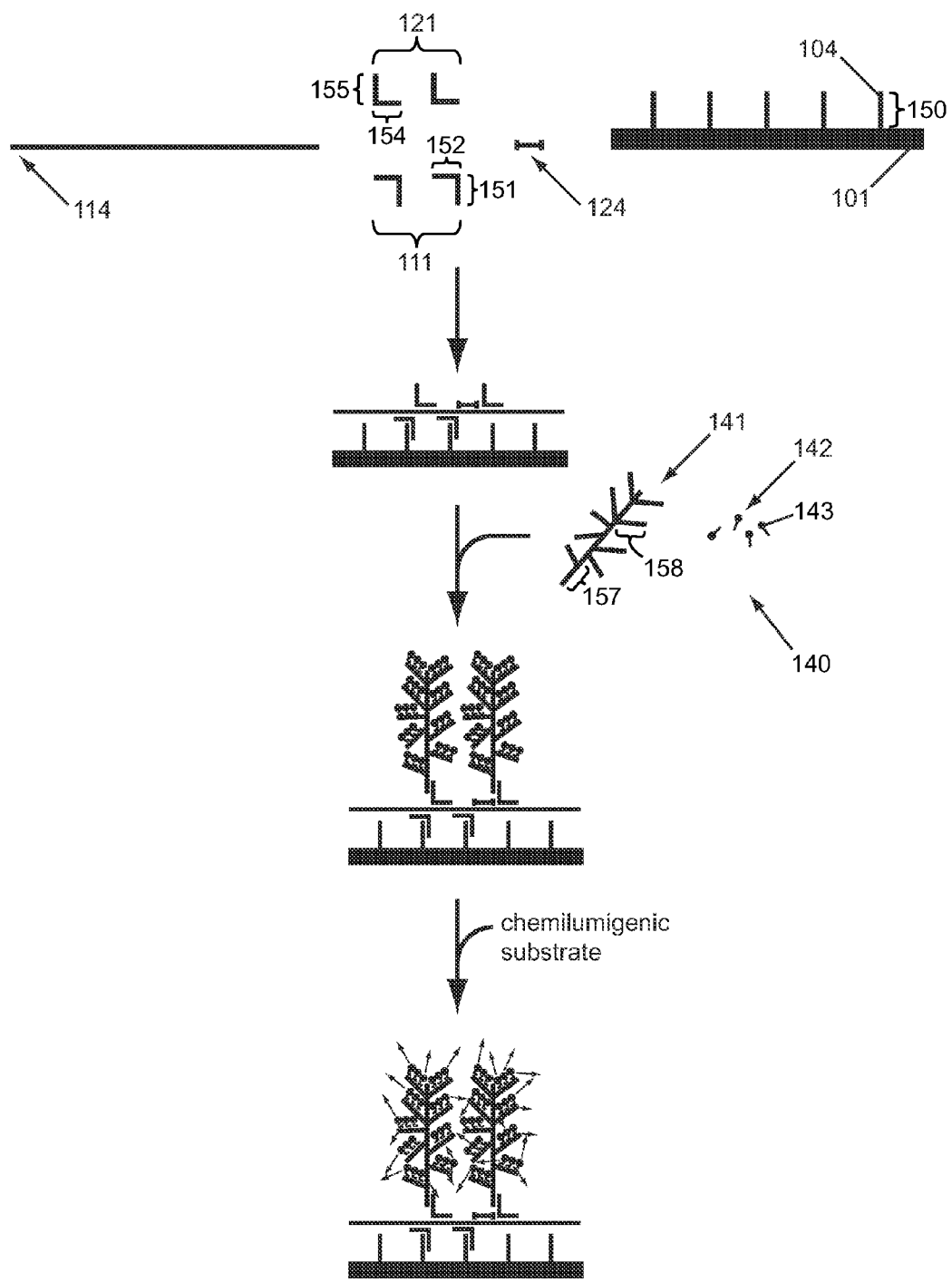
FIG. 4 shows a schematic diagram of an exemplary old art bDNA assay system.

Branched DNA Assays bDNA technology is useful in many embodiments of the present methods because it is compatible with in-situ and solid support chip analysis formats. An exemplary embodiment of bDNA technology is schematically illustrated in FIG. 4, wherein a single target nucleic acid strand is captured and detected as an accumulation of label probes. A cell or tissue sample is lysed to produce a lysate including target nucleic acid 114. The target nucleic acid 114 (e.g., an mRNA whose expression is to be detected) is captured by capture probe 104 on solid support 101 (e.g., a well of a microtiter plate) through set 111 of synthetic oligonucleotide capture extenders. Each capture extender has a first polynucleotide sequence C-3 (152) that can hybridize to the target nucleic acid and second polynucleotide sequence C-1 (151) that can hybridize to the capture probe through sequence C-2 (150) in the capture probe. Typically, two or more capture extenders are used; optionally, one CE can be used to capture a target. Each label extender in label extenders set 121 hybridizes to a different sequence on the target nucleic acid, through sequence L-1 (154) that is complementary to the target nucleic acid, and to sequence M-1 (157) on amplification multimer (141), through sequence L-2 (155). Blocking probes (124), which hybridize to sequences in the target nucleic acid not bound by either capture extenders or label extenders, are often used in bDNA assays to reduce non-specific target probe binding. A probe set for a given target nucleic acid in this example thus consists of capture extenders, label extenders, and optional blocking probes 124 for the target nucleic acid. The capture extenders, label extenders, and optional blocking probes are complementary to non-overlapping sequences in the target nucleic acid, and are typically, but not necessarily, contiguous. In this example, a single blocking probe is used; typically, an array of different blocking probes is used in an optimized bDNA assay.

Signal amplification can begin with the binding of the label extenders to the target nucleic acid. The amplification multimer is then hybridized to the label extenders. The amplification multimer has multiple copies of sequence M-2 (158) that is complementary to label probe 142. Label 143, for example, a fluorescent group, is covalently attached to each label probe. In the final step, labeled complexes are detected, e.g., by fluorometry. The amount of fluorescence can be proportional to the level of target nucleic acid originally present in the sample (a relationship describable, e.g., by a regression curve). When detecting two or more different target nucleic acids from the same sample, the typical old art bDNA assay provides only a combined result without separate identification or quantitation.

Basic bDNA assays have been well described and used, e.g., to detect taggants, to analyze forensic samples, to detect and quantify mRNA transcripts in cell lines, to determine viral loads, and the like. The bDNA assay provides reliable direct quantification of nucleic acid molecules under physiological conditions. Several advantages of the technology distinguish it from other DNA/RNA amplification technologies including, e.g., compatibility with complex samples, linear amplification, good sensitivity and dynamic range, great precision and accuracy, reduced sensitivity to laboratory sample cross contamination, simple sample preparation procedure, and reduced sample-to-sample variation. For additional details on bDNA assays, see, e.g., U.S. Pat. No. 4,868,105 to Urdea et al. entitled "Solution phase nucleic acid sandwich assay"; U.S. Pat. No. 5,635,352 to Urdea et al. entitled "Solution phase nucleic acid sandwich assays having reduced background noise"; U.S. Pat. No. 5,681,697 to Urdea et al. entitled "Solution phase nucleic acid sandwich assays having reduced background noise and kits therefore"; U.S. Pat. No. 5,124,246 to Urdea et al. entitled "Nucleic acid multimers and amplified nucleic acid hybridization assays using same"; U.S. Pat. No. 5,624,802 to Urdea et al. entitled "Nucleic acid multimers and amplified nucleic acid hybridization assays using same"; U.S. Pat. No. 5,849,481 to Urdea et al. entitled "Nucleic acid hybridization assays employing large comb-type branched polynucleotides"; U.S. Pat. No. 5,710,264 to Urdea et al. entitled "Large comb type branched polynucleotides"; U.S. Pat. No. 5,594,118 to Urdea and Horn entitled "Modified N-4 nucleotides for use in amplified nucleic acid hybridization assays"; U.S. Pat. No. 5,093,232 to Urdea and Horn entitled "Nucleic acid probes"; U.S. Pat. No. 4,910,300 to Urdea and Horn entitled "Method for making nucleic acid probes"; U.S. Pat. No. 5,359,100; U.S. Pat. No. 5,571,670; U.S. Pat. No. 5,614,362; U.S. Pat. No. 6,235,465; U.S. Pat. No. 5,712,383; U.S. Pat. No. 5,747,244; U.S. Pat. No. 6,232,462; U.S. Pat. No. 5,681,702; U.S. Pat. No. 5,780,610; U.S. Pat. No. 5,780,227 to Sheridan et al. entitled "Oligonucleotide probe conjugated to a purified hydrophilic alkaline phosphatase and uses thereof"; U.S. patent application Publication No. US2002172950 by Kenny et al. entitled "Highly sensitive gene detection and localization using in situ branched-DNA hybridization"; Wang et al. (1997) "Regulation of insulin preRNA splicing by glucose" Proc Nat Acad Sci USA 94:4360-4365; Collins et al. (1998) "Branched DNA (bDNA) technology for direct quantification of nucleic acids: Design and performance" in Gene Quantification, F Ferre, ed.; and Wilber and Urdea (1998) "Quantification of HCV RNA in clinical specimens by branched DNA (bDNA) technology" Methods in Molecular Medicine: Hepatitis C 19:71-78. In addition, reagents for performing basic bDNA assays (e.g., QuantiGene® kits, amplification multimers, alkaline phosphatase labeled label probes, chemilumigenic substrate, capture probes immobilized on a solid support, and the like) are commercially available, e.g., from Affymetrix, Inc. (on the world wide web at www.panomics.com), and can be adapted for the practice of the present invention. Software for designing probe sets for a given nucleic acid target (i.e., for designing the regions of the capture extenders, label extenders, and optional blocking probes that are complementary to the target) is also commercially available (e.g., Probe-Designer™ from Affymetrix, Inc.); see also Bushnell et al. (1999) "ProbeDesigner: for the design of probe sets for branched DNA (bDNA) signal amplification assays Bioinformatics 15: 348.

Preparation of Samples for In-Situ Detections

In order to provide access for probes into cells or tissues, the samples can be rendered permeable by appropriate treatments. In many cases, it is advisable to expose the sample to a protease and/or a lipase to digest away proteins and membranes that may be blocking access of probes to target nucleic acids. For example, samples may be exposed to Proteinase K at about 5 ug/ml at 37° C. or more for 10 minutes or more to enhance the ability of nucleic acid probes to contact and hybridize with target nucleic acids in-situ.

In samples where RNA is a nucleic acid of interest, it is often beneficial to inhibit RNase enzymes. For example, the sample can be treated with a protein denaturing chemical, such as phenol. Optionally, the methods include treatment with an RNase inhibitor, such as, e.g., human placenta RNase inhibitor protein.

To analyze formalin fixed paraffin embedded (FFPE) samples, cells and tissues are generally made permeable by protease treatments and extraction of paraffin. Sensitivity may be enhanced by extracting paraffin using xylene and graded alcohols, heat and detergents, or commercially available products, such as, e.g., EZDeWax™.

Solid Supports

In vitro detections typically take place on a solid support substrate. Essentially any suitable solid support can be employed in the methods. For example, the solid support can comprise particles such as microspheres (e.g., beads), a conduit surface, or it can comprise a substantially planar and/or spatially addressable support. Different nucleic acids are optionally captured on different distinguishable subsets of particles or at different positions on a spatially addressable solid support. The nucleic acids of interest can be captured at a solid support by any of a variety of techniques, for example, by binding directly to the solid support or by binding to a moiety bound to the support, or through hybridization to another nucleic acid bound to the solid support. Preferably, the nucleic acids are captured at the solid support through hybridization with capture probes and/or capture extenders.

In some embodiments of the invention, the solid support has a planar surface and is typically rigid. The planar surface can be, e.g., the surface of a slide or an interior surface of a compartment or well. Exemplary materials for the solid support include, but are not limited to, glass, silicon, silica, quartz, plastic, polystyrene, nylon, a metal, a ceramic, and nitrocellulose. The solid support can, e.g., be a multiwell plate or a glass slide with an array of capture probes laid out in a grid pattern at selected positions.

In embodiments involving assay of a large number of samples in parallel, or multiplexed embodiments wherein many target nucleic acids are assayed from the same sample at once, the nucleic acids (e.g., sample nucleic acids) can be captured at different positions on a non-particulate, spatially addressable solid support. Thus, in one class of embodiments, the solid support comprises two or more capture probes, wherein each capture probe is provided at a selected position on the solid support. Two or more subsets of "n" capture extenders can be provided, wherein n is at least two. Each subset of n capture extenders can be capable of hybridizing to one of the nucleic acids of interest, and the capture extenders in each subset can be capable of hybridizing to one of the capture probes, thereby associating each subset of n capture extenders with a selected position on the solid support. Each of the nucleic acids of interest present in the sample can be hybridized to its corresponding subset of n capture extenders and the subset of n capture extenders can be hybridized to its corresponding capture probe, thereby capturing the nucleic acid on the solid support at the selected position with which the capture extenders are associated. In some embodiments, sense and anti-sense strands of a nucleic acid of interest can be captured at the same location using closely adjacent capture probes or capture extenders.

In a class of multiplexed embodiments, a pooled population of particles constitutes the solid support. The population comprises two or more subsets of particles, and a plurality of the particles in each subset is distinguishable (e.g., by a detectable identification signal) from a plurality of the particles in every other subset. Typically, substantially all of the particles in each subset are distinguishable from substantially all of the particles in every other subset. The particles in each subset typically have associated therewith a different capture probe.

Essentially any suitable particles can be used, e.g., particles having distinguishable characteristics and to which capture probes can be attached. For example, in one preferred class of embodiments, the particles are microspheres (e.g., small beads). The microspheres of each subset can be distinguishable from those of the other subsets, e.g., on the basis of their fluorescent emission spectrum, their diameter, or a combination thereof. For example, the microspheres of each subset can be labeled with a unique fluorescent dye or mixture of such dyes, quantum dots with distinguishable emission spectra, and/or the like. As another example, the particles of each subset can be identified by an optical barcode, unique to that subset, present on the particles.

Microspheres are preferred substrates in certain embodiments described herein since they are generally stable, are widely available in a range of materials, surface chemistries and uniform sizes, and can be fluorescently dyed. Luminex Corporation (www.luminexcorp.com), for example, offers 100 sets of uniform diameter polystyrene microspheres. The micro spheres of each set are internally labeled with a distinct ratio of two fluorophores. A flow cytometer or other suitable instrument can thus be used to classify each individual microsphere according to its predefined fluorescent emission ratio. Fluorescently-coded microsphere sets are also available from a number of other suppliers, including Radix Biosolutions (www.radixbiosolutions.com) and Upstate Biotechnology (www.upstatebiotech.com). Alternatively, BD Biosciences (www.bd.com) and Bangs Laboratories, Inc. (www.bangslabs.com) offer microsphere sets distinguishable by a combination of fluorescence and size. As another example, microspheres can be distinguished on the basis of size alone, but fewer sets of such microspheres can be multiplexed in an assay because aggregates of smaller microspheres can be difficult to distinguish from larger microspheres.

Methods of analyzing microsphere populations (e.g. methods of identifying microsphere subsets by their size and/or fluorescence characteristics, methods of using size to distinguish microsphere aggregates from single uniformly sized microspheres and eliminate aggregates from the analysis, methods of detecting the presence or absence of a fluorescent label on the microsphere subset, and the like) are also well described in the literature. See, e.g., the above references.

Suitable instruments, software, and the like for analyzing microsphere populations to distinguish subsets of microspheres and to detect the presence or absence of a label (e.g., a fluorescently labeled label probe) on each subset are commercially available. For example, flow cytometers are widely available, e.g., from Becton-Dickinson (www.bd.com) and Beckman Coulter (www.) beckman.com). Luminex 100™ and Luminex HTS™ (which use microfluidics to align the microspheres and two lasers to excite the microspheres and the label) are available from Luminex Corporation (www.luminexcorp.com); the similar Bio-Plex™ Protein Array System is available from Bio-Rad Laboratories, Inc. (www.bio-rad.com). A confocal microplate reader suitable for microsphere and planar matrix analysis, the FMAT™ System 8100, is available from Applied Biosystems (www.appliedbiosystems.com).

The particles optionally have additional desirable characteristics. For example, the particles can be magnetic or paramagnetic, which provides a convenient means for separating the particles from solution, e.g., to simplify separation of the particles from any materials not bound to the particles.

Capturing Nucleic Acids

Target nucleic acids can be captured for analysis on any appropriate substrate. Note that for in-situ analyses, the nucleic acids of interest are typically already retained in a biomolecule matrix that holds the nucleic acids at a location, but allows access for hybridization with the probes.

In many methods of the invention, nucleic acids of interest are captured on a solid support (or in situ equivalent), e.g., in a step of the first and/or second amplification. The nucleic acids are typically in a purified or crude solution, allowing them to kinetically interact with groups associated with a solid support surface. The nucleic acids of interest can be captured directly or indirectly, specifically or non-specifically. In preferred embodiments, the nucleic acids are captured at the solid support indirectly (e.g., through capture extenders) with a high degree of specificity (e.g., under stringent hybridization conditions).

Nucleic acids of interest can be captured on a solid support directly and non-specifically. For example, the nucleic acids can be captured through chemical reactions or non-specific chemical interactions between the solid support and the nucleic acid. The solid support can include reactive groups that form covalent bonds to bases, or preferably the sugar-phosphate chain of the nucleic acid. The solid support can include chemical groups that interact with the nucleic acids through non-covalent forces, such as, e.g., ionic interactions, hydrophobic interactions, chelation, Van der Waals forces, polar interactions, and/or the like. A typical solid support for direct non-specific capture of nucleic acids can be, e.g., nitrocellulose or nylon membranes otherwise used in dot-blot, northern blot, or Southern blot analyses. Direct, non-specific capture is most appropriate, e.g., when the sample is relatively pure and/or the nucleic acid of interest is expected to be a predominant nucleic acid in the sample. In methods using direct, non-specific capture, it can be important to block the solid support, e.g., with sheared salmon sperm DNA and/or the like, to avoid generation of non-specific background signals.

In other embodiments, the nucleic acids of interest can be captured directly and specifically on a solid support. For example, the solid support can comprise a nucleic acid (e.g., capture probe) on the surface, which has sequences complementary to the nucleic acid of interest. Exposure of the nucleic acid of interest, in a sample solution adjusted to appropriate stringency, to a capture probe on the solid support can result in capture by specific hybridization directly with the solid support. Such an arrangement is capable of capturing the nucleic acid of interest from a complex sample, such as a lysate, even if the nucleic acid of interest represents only a small minority of the nucleic acids in the sample. Optionally, nucleic acids, (e.g., comprising haptens or protein binding sites) can be captured specifically and directly by nucleic acid binding proteins or antibodies.

In still other embodiments, the nucleic acid of interest can be captured indirectly and specifically. In a preferred embodiment, a single type of solid support has the flexibility to optionally capture various alternate nucleic acids of interest. Such a solid support can have a "universal" capture probe that can hybridize to any number of capture extender oligonucleotides having a sequence complementary to the capture probe sequence and designed to be specifically to a particular nucleic acid of interest. In this way, the nucleic acid of interest can be captured indirectly, through the capture extender, but specifically through hybridization to the complementary sequence of the capture extender. The solid support is universal and the capture extender provides specificity to indirectly captured nucleic acids.

Hybridizing Nucleic Acids

Hybridizations between complementary sequences of amplification reaction components can provide, e.g., the direct or indirect capture of target nucleic acids; the binding interactions of amplification multimers and/or label probes; retention of desired components while undesired materials are removed in stringent wash steps; accumulation of substrates for enzyme amplifications; and/or the like.

Nucleic acids "hybridize" when they specifically associate in solution appropriate conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes*, part I, chapter 2, "Overview of principles of hybridization and the strategy of nucleic acid probe assays," (Elsevier, New York), as well as Ausubel et al., eds., *Current Protocols*, a joint venture between Greene Publishing Associates, Inc. and John Wiley & Sons, Inc., (supplemented through 2003). Hames and Higgins (1995) *Gene Probes* 1, IRL Press at Oxford University Press, Oxford, England (Hames and Higgins 1) and Hames and Higgins (1995) *Gene Probes* 2, IRL Press at Oxford University Press, Oxford, England (Hames and Higgins 2) provide details on the synthesis, labeling, detection and quantification of DNA and RNA, including oligonucleotides.

Methods of the invention can be optimized for hybridization and washing stringency through empirical studies, or through calculations of preferred conditions. Stringent hybridization conditions are typically at a temperature near the melting temperature ($T_m$) of the complementary sequences involved. For example, in the context of the present invention, stringent conditions for a given solution are 10° C. or less below the $T_m$, 5° C. or less below the $T_m$, 3° C. or less below the $T_m$, 1° C. below the $T_m$, or at about the $T_m$ of the subject hybridized complements. The $T_m$ of a DNA-DNA duplex can be estimated using the following equation:

$$T_m(° C.)=81.5° C.+16.6(\log_{10}M)+0.41(\%G+C)-0.72(\%f)-500/n,$$

where M is the molarity of the monovalent cations (usually Na+), (% G+C) is the percentage of guanosine (G) and cystosine (C) nucleotides, (% f) is the percentage of formamide and n is the number of nucleotide bases (i.e., length) of the hybrid. See, Rapley and Walker, supra. The $T_m$ of an RNA-DNA duplex can be estimated as follows:

$$T_m(° C.)=79.8° C.+18.5(\log_{10}M)+0.58(\%G+C)-11.8(\%G+C)^2-0.56(\%f)-820/n,$$

where M is the molarity of the monovalent cations (usually Na+), (% G+C) is the percentage of guanosine (G) and cystosine (C) nucleotides, (% f) is the percentage of formamide and n is the number of nucleotide bases (i.e., length) of the hybrid. Id. Equations 1 and 2 are typically accurate only for hybrid duplexes longer than about 100-200 nucleotides. Id. The Tm of nucleic acid sequences shorter than 50 nucleotides can be calculated as follows:

$$T_m(° C.)=4(G+C)+2(A+T),$$

where A (adenine), C, T (thymine), and G are the numbers of the corresponding nucleotides.

In certain embodiments of the invention, all of the hybridizations of the amplification complex (e.g., amplification probe system) are designed to have melting temperatures within about 5° C. of each other. In other cases, all the melting temperatures are designed to be within about 3° C. or about 1° C. of each other. In other embodiments, the melting temperatures of hybridizations in the complexes are designed to have higher melting temperatures for hybridizations initiated early in am amplification and lower melting temperatures for hybridizations initiated later in the amplification process (e.g., with stringent washes between the hybridizations).

Blocking probes can optionally be hybridized to the nucleic acids of interest, e.g., in bDNA amplifications to reduce background in the assay. For a given nucleic acid of interest, the corresponding label extenders, optional capture extenders, and optional blocking probes are preferably complementary to physically distinct, non-overlapping sequences in the nucleic acid of interest, which are preferably, but not necessarily, contiguous. It can be desirable to include blocking probes in bDNA amplifications, which are complementary to all target nucleic acid sequences not hybridized to other components of the amplification system. The $T_m$s of the capture extender-nucleic acid, label extender-nucleic acid, and blocking probe-nucleic acid complexes are preferably greater than the temperature at which the capture extenders, label extenders, and/or blocking probes are hybridized to the nucleic acid, e.g., by 5° C. or 10° C. or preferably by 15° C. or more, such that these complexes are stable at that temperature. Potential CE and LE sequences (e.g., potential sequences C-3 and L-1) are optionally examined for possible interactions with non-corresponding nucleic acids of interest, LEs or CEs, the preamplifier, the amplification multimer, the label probe, and/or any relevant genomic sequences, for example; sequences expected to cross-hybridize with undesired nucleic acids are typically not selected for use in the CEs or LEs. See, e.g., Player et al. (2001) "Single-copy gene detection using branched DNA (bDNA) in situ hybridization", J. Histochem. Cytochem. 49:603-611 and U.S. patent application 60/680,976. Examination can be, e.g., visual (e.g., visual examination for complementarity), computational (e.g., computation and comparison of binding free energies), and/or experimental (e.g., cross-hybridization experiments). Capture probe sequences are preferably similarly examined, to ensure that the polynucleotide sequence C-1 complementary to a particular capture probe's sequence C-2 is not expected to cross-hybridize with any of the other capture probes that are to be associated with other subsets of particles or selected positions on the support.

Hybridized nucleic acid duplexes align antiparallel. In figures, where one nucleic acid strand is displayed in one orientation (e.g., 5' to 3' left to right), the complementary strand will be in the opposite orientation (e.g., 3' to 5'). In detection complexes, components in serial association are designed to alternate between these orientations. For example, where a capture probe is attached to a solid support from a 3' end with the 5' end extending away from the solid support, complementary capture extenders are typically designed to provide the complementary sequence on the 5' end, thus leaving the capture extender 3' end free of the solid support surface to capture a target nucleic acid. Similarly, if a label extender is designed with a complementary sequence at the 5' end intended to hybridize with a captured nucleic acid of interest (leaving the 3' LE end free), an amplification multimer complement strand will typically be designed with a 3' end sequence free to specifically hybridize to the free 3' end of the label extender.

The various hybridization and capture steps can be performed simultaneously or sequentially, in any convenient order. For example, in embodiments in which capture extenders are employed, each nucleic acid of interest can be hybridized simultaneously with its corresponding label extenders and its corresponding capture extenders in solution, and then the capture extenders can be hybridized with capture probes associated with the solid support. Materials not captured on the support are preferably removed, e.g., by washing the support, and then the label probe system is hybridized to the label extenders.

Washing Solid Supports

At any of various steps, materials not captured on the solid support are optionally separated from the support by washing. For example, after the capture extenders, nucleic acids, label extenders, blocking probes, and support-bound capture probes are hybridized, the support is optionally washed to remove unbound nucleic acids and probes; after the label extenders and amplification multimer are hybridized, the support is optionally washed to remove unbound amplification multimer; and/or after the label probes are hybridized to the amplification multimer, the support is optionally washed to remove unbound label probe prior to detection of the label. The support is optionally washed at the end of the first amplification to remove unbound labeled probes.

After hybridization steps in the methods, unhybridized nucleic acid material can be removed by a series of washes, the stringency of which can be adjusted depending upon the desired results. Low stringency washing conditions (e.g., using higher salt and lower temperature) can increase sensitivity, but can produce nonspecific hybridization signals and high background signals. Higher stringency conditions (e.g., using lower salt and a higher temperature that is closer to the hybridization temperature) lowers the background signal, typically with only the specific signal remaining. See, Rapley, R. and Walker, J. M. eds., *Molecular Biomethods Handbook* (Humana Press, Inc. 1998), which is incorporated herein by reference in its entirety for all purposes. "Stringent hybridization wash conditions" in the context of the amplification methods, are sequence dependent. An extensive guide to the hybridization of nucleic acids is found in Tijssen (1993), supra, and in Hames and Higgins 1 and Hames and Higgins 2, supra.

Solid Support Capture Arrays

An array of capture probes can be prepared on a solid support (e.g., a membrane, a glass or plastic slide, a silicon or quartz chip, a plate, or other spatially addressable solid support), typically with each capture probe bound (e.g., electrostatically or covalently bound, directly or via a linker) to the support at a unique selected location. Methods of making, using, and analyzing such arrays (e.g., microarrays) are well known in the art. See, e.g., Baldi et al. (2002) DNA Microarrays and Gene Expression: From Experiments to Data Analysis and Modeling, Cambridge University Press; Beaucage (2001) "Strategies in the preparation of DNA oligonucleotide arrays for diagnostic applications" Curr Med Chem 8:1213-1244; Schena, ed. (2000) Microarray Biochip Technology, pp. 19-38, Eaton Publishing; technical note "Agilent Sure-Print Technology: Content centered microarray design enabling speed and flexibility" available on the web at chem.agilent.com/temp/rad01539/00039489.pdf; and references therein. Arrays of pre-synthesized polynucleotides can be formed (e.g., printed), for example, using commercially available instruments. Alternatively, the polynucleotides can be synthesized at the selected positions on the solid support; see, e.g., U.S. Pat. No. 6,852,490 and U.S. Pat. No. 6,306,643, each to Gentanlen and Chee entitled "Methods of using an array of pooled probes in genetic analysis."

Suitable instruments, software, and the like for analyzing arrays to distinguish selected positions on the solid support and to detect the presence or absence of a label (e.g., a fluorescently labeled label probe) at each position are commercially available. For example, microarray readers are available, e.g., from Agilent Technologies (Palo Alto, Calif.), Affymetrix (Santa Clara, Calif.), and Zeptosens (Switzerland).

Label Systems

Label systems of the present methods are essentially as described above in the Compositions section. bDNA label systems include a sequence complementary to a target nucleic acid of interest and two or more sequences complementary to a label probe.

bDNA label systems include at least an amplification multimer and label probes. Optionally, label systems include one or more label extenders, or the amplification multimer can be complementary to and hybridize directly to the intended nucleic acid of interest. In a less preferred embodiment for most circumstances, the label system can simply consist of label probes (e.g., labeled oligonucleotides). The amplification multimers can be as described above, e.g., a natural or unnatural nucleic acid comprising multiple sequences complementary to label probe molecules, e.g., a branched DNA, a preamplifier strand associated with an amplifier strand, or a single un branched amplifier strand.

Typically, the label system sequence complementary to the target nucleic acid is a sequence on a label extender or amplification multimer. In multiplexing embodiments wherein the presence of two or more different target nucleic acids are detected as two or more different signals, label systems with different signals are associated with each different target through unique complementary sequences. The multiplexing amplification system can also have a second label extender complementary only to a second target and to a second amplification multimer, which has multiple sequence sites complementary to accumulate only those label probes having a second distinguishable signal. There can be third, fourth, and fifth signal sets of uniquely associating label extenders, amplification multimers and label probes, and so on. In this regard, a label system can include multiple uniquely associating sets with different distinguishable label signals to detect more than one target nucleic acid (and thereby, uniquely identify the presence of more than one nucleic acid of interest from a test sample). Such systems can be designed to detect two or more nucleic acids (e.g., double strands) at the same location.

Labels

Labels can provide the final highly amplified signal associated with the presence of a nucleic acid of interest in a sample. Moreover, labels can be provided with a range of distinguishable signals, e.g., useful in multiplexing and strandedness schemes of the invention.

A wide variety of labels are well known in the art and can be adapted to the practice of the present inventions. For example, luminescent labels and light-scattering labels (e.g., colloidal gold particles) have been described. See, e.g., Csaki et al. (2002) "Gold nanoparticles as novel label for DNA diagnostics" Expert Rev Mol Diagn 2:187-93.

As another example, a number of fluorescent labels are well known in the art, including but not limited to, hydrophobic fluorophores (e.g., phycoerythrin, rhodamine, Alexa Fluor® 488 and fluorescein), green fluorescent protein (GFP) and variants thereof (e.g., cyan fluorescent protein and yellow fluorescent protein), and quantum dots. See e.g., The Handbook: A Guide to Fluorescent Probes and Labeling Technologies, Tenth Edition or Web Edition (2006) from Invitrogen (available on the world wide web at probes.invitrogen.com/handbook), for descriptions of fluorophores emitting at various different wavelengths (including tandem conjugates of fluorophores that can facilitate simultaneous excitation and detection of multiple labeled species). For use of quantum dots as labels for biomolecules, see e.g., Dubertret et al. (2002) Science 298:1759; Nature Biotechnology (2003) 21:41-46; and Nature Biotechnology (2003) 21:47-51.

In certain aspects of the methods, the label is an alkaline phosphatase capable of interacting with any number of substrates to generate detectable fluorescent of colored compounds. For example, the fast red substrate in the presence of alkaline phosphatase enzyme can produce a red reaction product that can be seen, e.g., using either brightfield, fluorescent microscopy, or electronic imaging detectors. Optionally, the substrate can be fast blue, to impart a visible blue color to a location retaining the alkaline phosphatase probe label.

Alexa Fluor® dyes (Life Technologies Corporation, Carlsbad, Calif.) can be particularly useful labels in the compositions and methods herein. These fluorescent dyes are available covering the entire spectrum and match the principal output wavelengths of common excitation sources. Such color options can be particularly useful in embodiments herein wherein multiple probes are to be detected simultaneously.

Labels can be introduced to molecules, e.g. polynucleotides, during synthesis or by post-synthetic reactions by techniques established in the art; for example, kits for fluorescently labeling polynucleotides with various fluorophores are available from Molecular Probes, Inc. (www.molecularprobes.com), and fluorophore-containing phosphoramidites for use in nucleic acid synthesis are commercially available. Similarly, signals from the labels (e.g., absorption by and/or fluorescent emission from a fluorescent label) can be detected by essentially any method known in the art. For example, multicolor detection, detection of FRET, fluorescence polarization, and the like, are well known in the art.

Detecting Nucleic Acid Probes

Probes of the compositions and methods can be detected by various means to confirm the presence and nature of the target in the sample. For example, the probes can be detected by 280 nm absorbance, fluorometry in the presence of ethidium bromide, polyacrylamide gel electrophoresis, Southern blotting, northern blotting, and the like. In many embodiments, detection can be by visual inspection or using photographic detection.

The methods can optionally be used to quantitate the amounts of the nucleic acids of interest present in the sample. For example, in one class of embodiments, an intensity of a signal from the probe label is measured and correlated (e.g., through a standard formula determined through regression analysis) with a quantity of the corresponding nucleic acid of interest present. The standard formula can then be used to calculate an unknown amount of nucleic acid in a sample based on the output signal intensity for that sample.

The methods can be used to quantitatively detect nucleic acids of interest in samples, e.g., for gene expression analysis. Accordingly, in one class of embodiments, the one or more nucleic acids of interest comprise one or more mRNAs and/or DNA targets. A standard curve of, e.g., signal output from a detection versus signals from similar nucleic acids of known amounts can be prepared. For example, standards can be evaluated based on mitochondrial DNA or known RNA quantities (see, e.g., Nucleic Acid Quantitation from Tissue Slides, U.S. Pat. No. 7,968,327). The output signal associated with the one or more mRNAs can be compared to the standard curve to determine the amount of the mRNAs in an unknown sample (e.g., regression analysis), as is known in the art.

Reporter groups associated with probe of the invention can be detected using any hardware appropriate to the chosen in-situ environment, solid support, and/or label system. Where the detection takes place on a nitrocellulose membrane or tissue slide and the reporter is an enzyme, the detector can simply be, e.g., a technician visually inspecting the membrane for development of a chromogen. Where the reporter is a fluorophore and the probe is hybridized in-situ or on an array, hybridization to target can be visible detection, e.g., using a fluorescence microscope, array scanner, or imaging device. Where the solid support is a floor of a well in a multiwell plate and the label is a chemiluminescent enzyme, a sequential or parallel formatted plate reader can be appropriate. In embodiments wherein the solid support is a bead with an identification signal, the label signal is typically detected using a fluorometer associated with a flow cytometer or with a charge coupled device viewing the beads settled into a two dimensional array. These exemplary embodiments of appropriate detectors are not limiting and one skilled in the art would appreciate appropriate variations.

In methods for detecting, locating, and/or quantitating single and double stranded nucleic acids, the detector will typically include sensors responsive to two or more different signals from, e.g., sense and anti-sense probes. For example, the human eye can view an in-situ hybridization of a tissue through a fluorescence microscope and detect mRNA is a cell cytoplasm bound to a sense probe (e.g., blue emission signal) and also see the double stranded DNA gene that encoded the mRNA bound to both sense (blue) and anti-sense (e.g., yellow emission) probes as a green signal. Thus, a technician at a microscope can see the locations, character, and quantity of a dsDNA gene and its transcribed mRNA. Optionally, similar visualizations can be accomplished in vitro, e.g., in the context of a capture array or bDNA detection. Optionally, the detection is carried out by an imaging system or automated scanner, e.g., with images and/or data stored physically, e.g., on film or in a computer. Typically, in the present inventions, it is preferable that imaging systems are capable of color resolution.

Systems for Simultaneous Detection of DNA and RNA

Probe systems can be configured to selectively detect and distinguish between single and double stranded DNA and RNA, e.g., simultaneously in-situ. The character of detected nucleic acids can be elucidated by adjusting the quantity and proportion of probes to the advantage of a DNA target over an RNA target, e.g., by selecting probe sequences that favor either DNA or RNA, by using DNA and RNA probes with different signals, and/or by using sense and anti-sense probes with different signals.

In the context of in-situ hybridization of cells and tissues, we have found that DNA and RNA can be distinguished by the proportionately stronger signals resulting from RNA hybridizations over DNA hybridizations, e.g., even where target sequences are the same. That is, e.g., a probe to a coding sense strand of a genomic DNA will provide a weaker signal than the same probe against a transcribed mRNA copy of the DNA. Without being bound to a particular theory, this proportional signal result may be due to the relatively difficult access of the probe to the DNA sense strand as compared to mRNA access. For example, hybridization to the DNA can be hindered by the cell nucleus location, the double stranded nature of the DNA, the DNA being surrounded by associated proteins such as histones, and/or by the DNA having less freedom of movement. The present systems can take advantage of this signal difference to distinguish between DNA and RNA in an in-situ hybridization of cells or tissues.

In an aspect of the invention, the mass action of DNA probes in the present systems can be designed to be proportionately greater than for the RNA probes. For example, the proportion of individual DNA probes is at least 2-fold, 3-fold, 5-fold, 7-fold, 10-fold, 20-fold, or more, than individual RNA probes in the probe systems. That is, where DNA is probed with a hybridization solution containing 9,000 copies of a single type (i.e., having the same complementary target sequence) of DNA probe, the hybridization solution would include at least, e.g., 3-fold less (3,000 or fewer) copies of RNA probe.

In another aspect, the number of different DNA probes is proportionately greater than for the RNA probes in the present probe systems. For example, the number of different (i.e., having different DNA target sequence complements) DNA probes can be at least 2-fold, 3-fold, 5-fold, 7-fold, 10-fold, 20-fold, 50-fold, or more, than the number of different RNA probes in the systems. That is, where DNA is probed with a hybridization solution containing 60 different DNA probes, the hybridization solution would include at least 3-fold less (20 or fewer) different of RNA probes.

In yet another aspect, the footprint of the DNA probe coverage can be proportionately greater than the coverage provided by the RNA probes in the system. For example, the total bases covered on the target DNA by the DNA probes can be at least 2-fold, 3-fold, 5-fold, 7-fold, 10-fold, 20-fold, 50-fold, 100-fold, or more, than the coverage of the RNA probes in the systems. That is, where DNA target is probed with a hybridization solution containing enough different DNA probes to rise above background signal and having a total footprint coverage at least, e.g., 3-fold more than the total target RNA sequence covered by the RNA probes in the hybridization. For example, where the total length of DNA targeted by probes is 3 kilobases, the total length of RNA targeted would include not more than about 1 kilobase.

In the above examples, it is often preferred that the DNA probes and RNA probes have similar affinity (e.g., Tm) for their target sequences. This enhances the ability to obtain optimum signal strength and reduced background when the full probe system is hybridized with the same level of hybridization stringency. That is, it is preferred that the different probes in the system have similar melting temperatures. It can be preferred that the target binding sequences have similar sequence lengths. It can be preferred that the target binding sequences have similar sequence GC %. With consideration of target sequences, probe length and GC % can be adjusted to provide a system of probes within a narrow functional range of melting temperatures.

DNA Probe Sets

DNA probe sets of the systems can beneficially have at least 3-fold more absolute numbers, at least 3-fold more different target sequences, and/or at least 3-fold more target coverage than the RNA probes of the systems for simultaneous detection of DNA and RNA in-situ. DNA probe sets can range from more than 1000 different probes (not counting blocking probes) to 5 probes, 300 different probes to 10 probes, 250 different probes to 25 probes, or about 100 different probes. In the context of bDNA probes, each different probe covers about 50 to 10 bases, or about 25 bases. DNA probe sets can be configured to cover 50 kilobases (kb) or more of target sequence to about 1 kb or less, from 25 kb to 2 kb, from 15 kb to 5 kb, or about 10 kb. For example, a typical DNA probe set of the system can have at least 100 different DNA probes covering at least 2 kilobases of DNA target.

In addition, the DNA probes of the system can have a reporter group that emits signals different from those of the RNA probe set. For example the DNA probe set of the systems can have a reporter enzyme, chromogen, radioactive nuclides, and/or fluorophores, that provide a first signal, and the RNA probe set can provide a second signal different from the first. This can aid in simultaneous detection and resolution of DNA and RNA in the same sample.

In some embodiments, it can be beneficial to employ mass action to drive up the DNA signal and/or help distinguish between DNA and RNA targets. For example, the concentration of DNA probes can be greater than the concentration of RNA specific probes.

To further enhance the sensitivity and specificity of simultaneous DNA and RNA analysis in-situ, the DNA probes can include sequences not normally found in the RNA target of interest. For example, while mRNA may include sequences corresponding to the DNA sense strand of a gene, it would not be expected to have sequences associated with the anti-sense strand. Therefore, in certain embodiments, the DNA probe set will include sequences targeting the anti-sense strand of the gene of interest, while the RNA probe targets the mRNA sequences, e.g., coding sequences of the sense strand. In some cases, members of the DNA probe set include probes targeting intron sequences of a gene of interest.

RNA Probe Sets

RNA probe sets of the systems can beneficially have one third or less in absolute numbers of probe molecules, one third or less different target sequences, and/or one third or less target coverage than the DNA probes of the systems for simultaneous detection of DNA and RNA in-situ. RNA probe sets can range from more than 200 different probes (not counting blocking probes) to 1 probe, 100 different probes to 3 probes, 50 different probes to 5 probes, or about 20 different probes. RNA probe sets can be configured to cover 10 kilo bases or more of target sequence to about 30 bases or less, from 5 kb to 100 bases, from 500 bases to 200 bases, or about 300 bases. For example, a typical RNA probe set of the system can have about 25 different RNA probes covering about 400 bases of RNA target.

In addition, the RNA probes of the system can have a reporter group that emits signals different from those of the DNA probe set, as described above. Further, the DNA and RNA probe sets can include reporters of different types, e.g., DNA probes with a fast blue chromogen and RNA probes with an FITC fluorophores.

The RNA probes can include sequences not normally found in the DNA target of interest. For example, mRNA may include sequences corresponding to splices between DNA coding sequences, e.g., continuation of 5' and 3' introns with the intervening intron removed. Such contiguous sequences do not appear in the gene sequence.

Detection Devices

Detection devices of the systems can be any appropriate to the reporter(s) of the probe systems, e.g., as discussed above.

For example, detectors can include photographic film, digital cameras, scanners, microscopes, phosphoimagers, and/or the like. In a typical system for simultaneous detection of RNA and DNA in-situ, the reporter is a chromogen or fluorophore detectable with sensitivity and precision using a microscope, e.g., in combination with fluorescent excitation and/or a CCD detector.

Methods for Simultaneous Detection of DNA and RNA

The methods for simultaneous detection of DNA and RNA in-situ take advantage of, e.g., differences in target sequences and hybridization kinetics to readily distinguish and resolve the nucleic acids at a microscopic level. A method for detecting DNA or RNA in-situ can include providing a DNA specific probe set, and providing an RNA specific probe set, e.g., comprising fewer probes than the DNA claim set. Signals from these probe sets can be inferred, e.g., by location and signal intensity, but it is preferred that the two probe sets have reporters with different distinguishable signals. A sample of interest, putatively containing DNA and/or RNA molecules or sequences of interest, can be simultaneously hybridized with the DNA probe set and RNA probe set. Finally, the sample can be examined with an appropriate detector, e.g., to determine the character, location, and/or quantity of DNA and RNA of interest in the sample.

Developing a DNA Probe Set

Providing a DNA probe set can be as discussed above. For example, a DNA probe set can be adapted to provide a signal above background upon hybridization with the sample of interest. In many cases, an adequate signal from hybridization of target DNA in-situ in, e.g., a fixed cell or tissue sample, can be obtained with a set of probes (e.g., label extenders and associated bDNA amplification complex) comprising at least 10 different probes covering at least 200 base pairs of the DNA target sequence. For example, the DNA probe set can functionally include at least 10 different probes, at least about 20 different probes, at least about 40 different probes, at least about 60 different probes, at least about 100 different probes, at least about 500 different probes or more. The DNA probe set can functionally include different probes targeting coverage (sequence specific hybridization) totaling at least 100 bases of the target DNA, at least 200 bases, at least 500 bases, at least 1000 bases, at least 2 kilobases, or more.

Methods can include a step of determining parameters to obtain DNA specific signal visible above background. For example, for a given sample, such as FFPE tissue on microscope slides, a series of DNA probe sets can be prepared including increasing numbers of different probes and/or increasing target sequence coverage. Tissue samples can be hybridized with each probe set and a probe number and/or coverage level identified wherein the DNA signal rises above background. For example, the number of different probes and/or coverage can be identified wherein the signal from a gene of interest is at lease 2-fold over background, 3-fold, 5-fold, or more over background signals. In many embodiments, the number and/or coverage of the RNA probe set can be adjusted to a value below (e.g., 3-fold below or more) those of the DNA probe set. In this way, a signal from the RNA probe set can be confirmed as an RNA signal and not a DNA signal.

Developing an RNA Probe Set

Providing an RNA probe set can be as discussed above. For example, an RNA probe set can be adapted to provide an RNA signal above background upon hybridization with the sample of interest, e.g., while remaining at levels low enough not to present a signal above background in association with any complementary DNA that may be in the cell or tissue sample.

In many cases, an adequate signal from hybridization of target RNA in-situ in, e.g., a fixed cell or tissue sample, can be obtained without also raising a DNA signal (e.g., mRNA probe false positive to the corresponding DNA sense strand) with a set of probes comprising not more than 100 different probes covering not more than 2000 base pairs of the DNA target sequence. For example, the RNA probe set can functionally include less than 100 different probes, not more than about 75 different probes, not more than about 50 different probes, not more than about 25 different probes, not more than 10 probes, not more than 5 probes, not more than 3 probes, or one probe. The RNA probe set can functionally include different probes targeting coverage (sequence specific hybridization) totaling 3000 bases or less of the target RNA, less than 1000 bases, less than 600 bases, less than 300 bases, less than 60 bases, or 21 bases, or less. Design of RNA probe sets should consider the quantity and quality of the associated DNA probe set, e.g., ensuring that the RNA probe set has at least 3-fold less different probes and/or coverage.

Methods can include a step of determining parameters to obtain RNA specific signal visible just above background. With such parameters, the RNA probe set can be adjusted to be visible in association with the intended RNA target, but not present enough signal to be seen in association with complementary DNA sequence that may exist in the cell or tissue sample. For example, for a given sample, such as fixed lawn of cells in a 96-well plate, a series of RNA probe sets can be prepared including decreasing numbers of different probes and/or decreasing target sequence coverage. The cell samples can be hybridized with each probe set and a probe number and/or coverage level identified wherein the RNA signal is not detectable above background. For example, the number of different probes and/or coverage can be identified wherein the signal from a RNA target sequence of interest is not more than 2-fold over background, 3-fold, 5-fold, or more over background signals. In many embodiments, the number and/or coverage of the RNA probe set can be adjusted to a value readily detectable against background (e.g., 3-fold above or more) for the target RNA, but not provide a detectable false positive DNA signal. In this way, a signal from the RNA probe set can be confirmed as an RNA signal and not a DNA signal.

Additional Parameters to Enhance Resolution

Additional strategies can be combined with the background threshold techniques above to further enhance discrimination of DNA from RNA in a sample.

The DNA and RNA probe sets can have different reporters with separately identifiable output signals. For example, the DNA and RNA probe sets can have reporters of different type, e.g., a colored label and a fluorescent marker, a chemiluminescent marker and/or a nuclide. In such cases, the two signals can be immediately visually apparent at the same time, or the sample can be over laid with a record (e.g., exposed film or electronic projection) of one signal while viewing the second signal simultaneously in real time.

In a more typical example of the inventive methods, the reporters are of the same type, but the reporters output a measurable different signal. For example, chromogen labels can absorb different colors, or fluorescent labels can absorb or emit light of different wavelengths. In such a case, e.g., DNA probes emit yellow light, while probes RNA may emit red light. Such difference are readily observed and photographed to identify the location and/or quantity of target nucleic acids.

The double stranded nature of most DNA and the single stranded nature of most RNA can be used to help distinguish between DNA and RNA in the samples. According to one strategy, the RNA probe set may include reporters with a first signal, while the DNA probe set will include a combination of two different reporters (providing, e.g., the first signal and a second signal). For the DNA probe set, the first signal reporter can be on probes specific to a sense strand, and the second signal reporter can be on probes specific to the anti-sense strand. Only DNA will provide a mixed signal while RNA will only provide the first signal. In this way, even if the RNA probes may also hybridize with the DNA, the mixed signal will still suggest DNA at the location.

Resolution of DNA and RNA can be enhanced by ensuring that the DNA probe set does not include sequences normally transcribed into RNA. For example, the DNA probe set can avoid sequences predominantly from polypeptide encoding sections of a gene. DNA probe sets, e.g., specific to a gene, can include introns, anti-sense, and regulatory sequences. It is preferred that DNA probes and RNA probes are not complementary to the extent they can hybridize with each other under the conditions of the planned assay.

The location of a signal can help corroborate the type of nucleic acid bound by a probe. In addition to the indicators we have described, the nature of a tagged nucleic acid can be confirmed by the location of the signal, e.g., in a cell or tissue sample. For example, a signal, particularly a double stranded (mixed color) signal from the nucleus of a cell is more likely to indicate the presence of DNA. On the other hand, signals from the cytoplasm, or at the outer nuclear membrane, are more likely to indicate the presence of RNA. In many cases, even without stained background cells, or any image at all of the in-situ structures, the shape and dispersion of signals can indicate whether it comes from the nucleus (e.g., round, ball, or spherical shape) or the cytoplasm (e.g., donut, ring, torus, or shape with a hole). Interpretation of signal location and shape can enhance the specificity of RNA/DNA detections.

Methods to distinguish RNA from DNA in a sample can include combinations of the techniques described above. For example, a DNA probe set can be prepared with 50 or more different probes covering 800 or more base pairs. The DNA probe set can include anti-sense and intron sequences and include both red and blue reporters. The RNA probe set can include 30 or less different probes covering 600 or less bases. The RNA probe set can include mRNA and exon sequences and include yellow reporters. In such a case, the target DNA locations would have a strong enough signal to rise above background, e.g., with a violet mixed signal, while any RNA would be visible as a yellow signal.

Simultaneous Hybridization

Simultaneous hybridization of RNA and DNA can be effectively carried out in the present methods. In the prior art there may be methods wherein a sample is first interrogated by hybridization with a first probe and detected, then the sample is melted and prepared for hybridization to a different probe, in sequence. Here, we have described techniques allowing simultaneous hybridization and unique detection of DNA and RNA is the same sample, e.g., even if the include the same or similar target sequences.

Samples can be treated to enhance the permeability of probes into cells. For example, cells and tissues in-situ can be treated with proteases, lipases, heat, and/or fat dissolving solvents, as is known in the art.

Samples can be pretreated to block non-specific binding and to reduce background when the samples are detected. For example, the samples can be blocked with a hybridization solution, e.g., containing carrier nucleic acids (e.g., salmon sperm DNA) and/or albumin.

The hybridization solution can be formulated, as is well known in the art, to include non-specific binding blockers, and elements that influence the melting temperature of hybridized nucleic acids. For example, see the Hybridizing Nucleic Acids section above. The hybridization solution can receive all probes, e.g., the DNA probe set and RNA probe set, for hybridization of the sample at once. The quantities and proportions of probes should be incorporated according to the discussions above. For example, the number of different probes and/or total target coverage of the DNA probe set should be greater than for the RNA probe set, as discussed above. In preferred embodiments the number of different probes and the total target coverage of the DNA probe set are greater than for the RNA probe set.

Simultaneous Detection

Detection of the in-situ hybridizations can be by any appropriate means, e.g., as described above. Typically, detections are of light, e.g., in the visible, or near visible range. Although large amounts of probe hybridized DNA or RNA can be macroscopically visible detections typically employ microscopic enlargement of the in-situ terrain for viewing directly by eye or through an electronic imaging system.

In some embodiments, the presence or absence of DNA or RNA of interest in a cell can be determined using flow cytometry. The same basic mechanisms of distinguishing between DNA and RNA described above apply in this context. After simultaneous hybridization, sample cells can be suspended and made to flow past detectors to determine, e.g., the specific DNA, RNA, strandedness, location, and/or quantity of nucleic acids of interest in the cells.

Depending on, e.g., the area and/or intensity of signals, the quantity of nucleic acids of interest can be determined. For example, where the strength of a signal from one of more probe is known, the amount in a sample, or sample location, can be determined according to a correlation equation (e.g., regression analysis), as discussed above.

EXAMPLES

The following examples are offered to illustrate, but not to limit the claimed invention.

Most viruses have double- or single-stranded RNA (ss-RNA) genomes and/or produce long dsRNA helices during transcription and replication; the remainder of viruses have DNA genomes and typically produce long dsRNA via symmetrical transcription. In contrast, uninfected mammalian cells generally do not produce long dsRNA (e.g., greater than 21-23 base pairs). Natural cellular defenses exploit this difference in order to detect and to attempt counter viral infections.

The presence of dsRNA can be detected using a bDNA method, such as the QuantiGene® assay. An advantage of bDNA assay in this context is that RNA can be measured directly from the sample source, without RNA purification or enzymatic manipulation, thereby avoiding inefficiencies and variability introduced by or errors inherent to these processes.

In a variant of the bDNA assays, the presence of a dsRNA (or dsDNA) can be confirmed using paired (sense/anti-sense) probes of different colors. For example, a sample can be exposed to one probe set (green) that binds toward the 5' end of the anti-sense strand and another probe set (red) that binds toward the 5' end of the sense strand. Only dsRNA will emit fused signal (yellow).

Example 1

Identifying Double Stranded Nucleic Acids on a Solid Support

The presence of a double stranded nucleic acid in solution can be confirmed by capturing the nucleic acid on a solid support, e.g., with a capture extender sequence that binds the antisense strand and a label extender that binds sense strand at different location.

For example, as shown in FIG. 1, first strand 10 can be captured on substrate 11 by specific hybridization with capture extender 12. The first strand remains associated with the second strand through at least a segment of base pairing in a double stranded segment 13.

A label system 14 is introduced with a sequence specifically complementing a second strand sequence through label extender 18. If the second strand is associated with the captured first strand, then a reporter signal, e.g., from label probes 15 will be detected at the solid support location. If the second strand is single stranded and not associated with the first strand, there sill be no signal at the solid support location. In this way, the presence of a particular double stranded nucleic acid can be detected in a solution.

Figure 2:
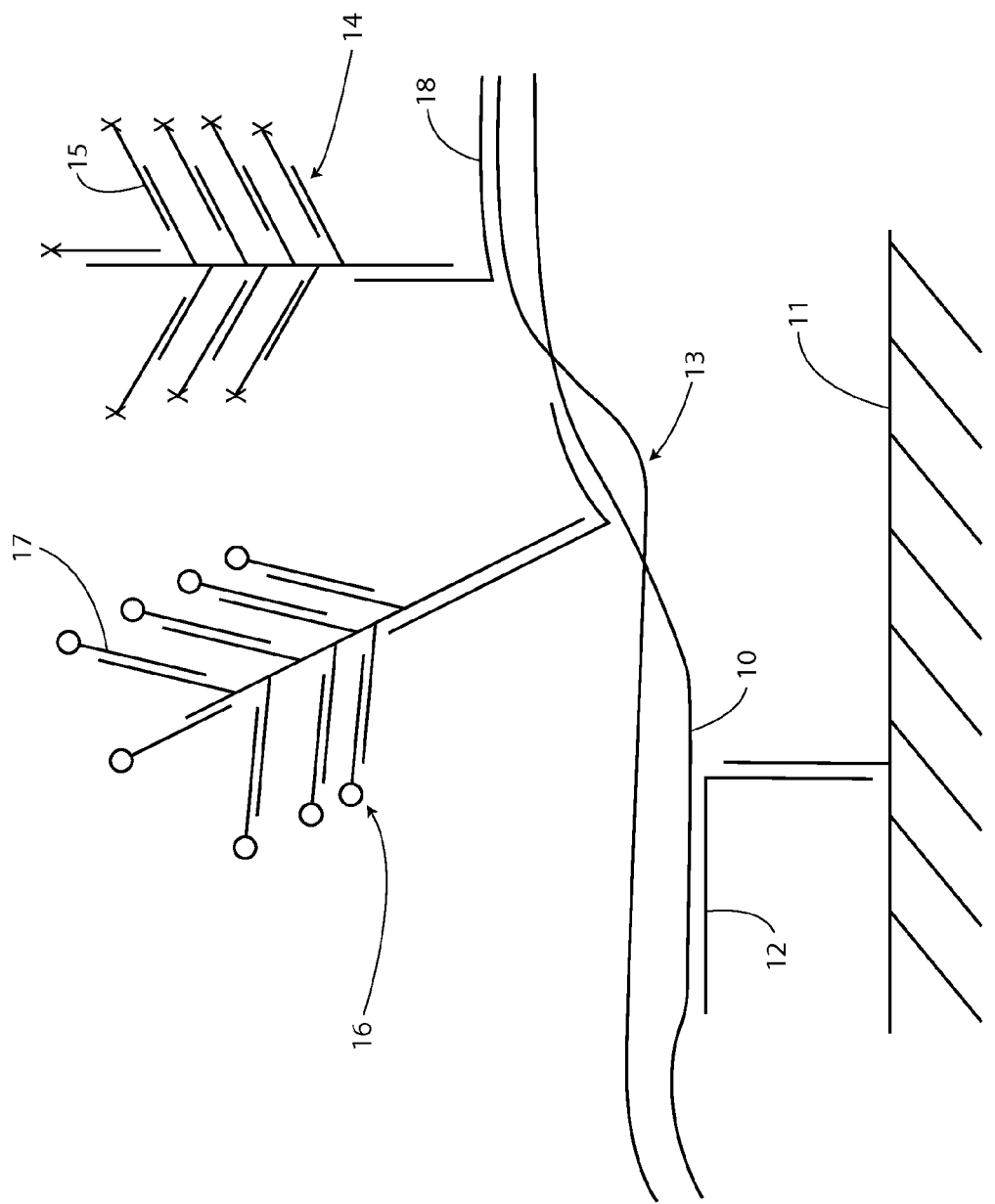
FIG. 2 shows a schematic example of double stranded nucleic acid detection on a solid support, using a first strand capture while using a first strand probe signal and a second strand probe signal to confirm double stranded status of the captured nucleic acid.

In an alternate embodiment, shown in FIG. 2, the presence of the double stranded nucleic acid can be detected with a higher level of specificity by including a second label system 16. The label probes 15 of the first label system can provide a reporting signal different from the reporting signal of label probes 17 of the second label system. Double stranded character is confirmed where signals from both the first and second label probes are detected from the same solid support location.

In this dual probe embodiment, the reporting signals can be configured to complement aided or unaided human vision. For example, the first probe 15 can be designed to fluoresce red, and the second probe 17 designed to fluoresce green. The first nucleic acid strand may be captured by capture extender 12 to provide a green signal at the location on hybridization with the second label system 16. If first label system 14 is also provided, there will also be a red signal from the location, if second nucleic acid strand 13 is associated with the first strand, e.g., through base pair bonding. In such a case, the color yellow (green plus red) would be apparent to a human eye at the location. If only the single stranded first strand were present, the human eye would perceive the color red at the location.

Example 2

Identifying Particular Double Stranded Nucleic Acids In-Situ

Here we describe compositions and methods for, e.g., identifying whether a hybridization signal is for a single, or double stranded nucleic acid, RNA or DNA, e.g., in a fixed tissue sample.

In-situ hybridization, e.g., probing for nucleic acids in a fixed tissue sample, suffers from the problem that certain probes can hybridize to either a DNA coding sense strand or its transcribed mRNA. In other situations, such as in the field of double stranded RNA viruses, one would like to know if an RNA in a tissue sample is double stranded.

One advantage of in-situ hybridization can be that nucleic acids in fixed samples tend to remain localized. Therefore, e.g., the tissue matrix can act as a substrate, retaining nucleic acids at a particular location. Further, in an assay for double stranded nucleic acids, the strands do not have to remain base-pair bonded in order to test for double stranded status. That is, as compared to a solution or chip assay, it is not necessary to avoid melting or provide rehybridization conditions in order to carry out the following in-situ assay. Even with melting, the information of double strandedness and location is not lost.

An in-situ assay to determine the presence of a double stranded nucleic acid can be practiced, as follows. The double stranded nucleic acid 30 can be hybridized to first label system 31 on first strand 32 in a fixed tissue section sample. The double stranded nucleic acid can also be hybridized to second label system 33 on second strand 34. The first label system can have a different reporter signal than the second label system. If a detector detects signals from both label systems at a particular location, this suggests the location has the nucleic acid of interest in double stranded form. If a particular location of the tissue sample includes only one signal, the location has only one of the two strands of nucleic acid.

In a particularly useful embodiment, the first and second label systems emit signals in a wavelength visible to the human eye. As discussed above, the presence of both nucleic acids strands at a location will then be detected as mixed light frequencies, observed as a color different from either of the label systems alone.

Example 3

Simultaneous Detection of DNA and RNA in an In-Situ Sample

Oligonucleotide probe can hybridize to both RNA and DNA in-situ hybridization assay. Hence the DNA signals can be mistaken for an RNA signal, and vice versa. Genomic DNA signal is expressed in nucleus while RNA is expressed mostly in the cytoplasm. However, RNA can be also be expressed in the nucleus (e.g., inducible IL-8, non-coding RNA, transient mRNAs). Of particular concern are possibly mixed signals from coding DNA and the associated mRNA transcript.

We have designed strategies that used alone, or optionally in combination, can ensure specific detection of RNA and DNA, without confusion. Specific probe sets and procedures can distinguish DNA and RNA in-situ, even where they share common sequences. For example, probe sets can be prepared to take advantage of differences in target sequences, target size, strandedness, signal intensity, and/or target access to distinguish DNA from RNA in-situ.

We have found, e.g., in the context of certain bDNA in-situ hybridizations, that 30 LE pairs covering region less than 1.5 kb, can generate bright RNA signal (signal to background greater than 5), while the same DNA signal cannot be generated using less about 100 LE pairs covering 2 kb of target. DNA targets are typically larger, double stranded, include non-coding sequences, can be optically obscured, and obstructed by cell structures and histones. DNA probes can be designed to accentuate these differences over typical RNA targets. For example, DNA probe sets can be designed to:

Bind to the anti-sense sequence of targeted DNA.

Complement intron or other non-coding region of the target DNA.

Cover a large amount of the target sequence, e.g., 50 kilobases or more.

Include probes complementary to a large number of different sequences on the DNA target, e.g., using 100 probes, or more.

Include paired probes that confirm double stranded status.

RNA targets are typically smaller, often single stranded, include mostly coding sequences, optically less obscured, and are less obstructed by cell structures and macromolecules. Exemplary RNA probe sets can be designed to:

Include sequences, such as coding sequences intended to bind to the sense sequence.

Cover a relatively small amount of the target sequence, e.g., less than 1.5 kilobases.

Include probes complementary to a relatively small number of different sequences on the target, e.g., using 30 probes, or less.

These parameters can of course vary. One basic concept is DNA and RNA in a tissue or cell can be distinguished by adjusting the relative intensity of interrogation of the probes so that the DNA target and RNA target will each be detectable (e.g., 3-fold over background). Because the DNA is typically is detected with less sensitivity, the DNA detection system is provided with qualitative and/or quantitative probe advantages, e.g., so that it can be detected on par with the RNA target of interest. For example, for a tissue sample, the DNA probe set can include, e.g., 3-fold more different probes than the RNA probe set, a more intense or more readily detectable reporter group, and/or cover at least 5-fold more of the target sequence.

In one aspect, DNA can be distinguished from RNA in-situ by the signal intensity relative to a standard reference. For example, the probe systems can include a reference probe set targeting a relatively stable target such as, e.g., mitochondrial DNA, ribosomal RNA, or a consistently expressed gene, such as GAPDH. Based on the standard signal, signals above a certain level can be considered RNA signals and signals below the level can be considered DNA signals. This technique can distinguish DNA and RNA, even if the probes have the same coding sequences.

DNA and RNA signals can be distinguished with higher levels of sensitivity and specificity by considering combinations of parameters. For example, techniques described above can be combined with the strategy of employing sense and anti-sense probe pairs of different colors, e.g., so that DNA (typically double stranded) will be detected as a combined color (e.g., red and yellow to make orange). For example, the above described techniques can be combined with the approaches of having different reporters (e.g. probe colors) from DNA and RNA probes, using microscopy to identify the location (e.g. nucleus versus cytoplasm) of probe signals, and/or employing RNA probes to encoding regions and DNA probes to non-coding regions (e.g., of the same gene).

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for simultaneous detection of DNA and RNA in situ, the method comprising:
    providing a first set of label extenders capable of hybridizing to a DNA sequence;
    providing a second set of label extenders capable of hybridizing to an RNA sequence;
    wherein the first set includes at least three times as many different label extenders as the second set;
    providing a sample comprising a cell, wherein the cell comprises the DNA sequence and the RNA sequence;
    simultaneously hybridizing the label extenders of the first set to the DNA sequence and the label extenders of the second set to the RNA sequence in the cell;
    binding multiple copies of a first label to the first set of label extenders;
    binding multiple copies of a second label to the second set of label extenders;
    wherein the first label provides a first detectable signal and the second label provides a second detectable signal that is distinguishable from the first signal; and
    detecting and distinguishing the first and second signals, thereby detecting and distinguishing the DNA and RNA sequences.

2. The method of claim 1, wherein the first set includes 50 or more different label extenders and the second set includes 16 or fewer different label extenders.

3. The method of claim 1, wherein the DNA sequence encodes the RNA sequence.

4. The method of claim 1, wherein said detecting comprises viewing the sample through a microscope.

5. The method of claim 1, wherein binding multiple copies of a first label to the first set of label extenders comprises hybridizing a first preamplifier to each label extender of the first set and to a plurality of copies of a first amplification multimer and hybridizing a plurality of copies of a first label probe that comprises or is configured to bind to the first label to each copy of the first amplification multimer; and wherein binding multiple copies of a second label to the second set of label extenders comprises hybridizing a second preamplifier to each label extender of the second set and to a plurality of copies of a second amplification multimer and hybridizing a plurality of the copies of a second label probe that comprises or is configured to bind to the second label to each copy of the second amplification multimer.

6. The method of claim 1, wherein the number of nucleotides of the DNA sequence to which the label extenders of the first set collectively hybridize is at least three times greater than the number of nucleotides of the RNA sequence to which the label extenders of the second set collectively hybridize.

7. The method of claim 3, wherein at least part of the DNA sequence to which the label extenders of the first set hybridize is identical to at least part of the RNA sequence to which the label extenders of the second set hybridize.

8. The method of claim 3, wherein the label extenders of the first set hybridize to one or more of intron sequences, anti-sense sequences, and non-coding sequences.

* * * * *